United States Patent
Desai et al.

(10) Patent No.: US 10,864,158 B2
(45) Date of Patent: Dec. 15, 2020

(54) MULTILAYER THIN FILM DRUG DELIVERY DEVICE AND METHODS OF MAKING AND USING THE SAME

(75) Inventors: Tejal A. Desai, San Francisco, CA (US); Mark Rory Steedman, San Francisco, CA (US); Robert Bhisitkul, San Francisco, CA (US); Daniel A. Bernards, San Francisco, CA (US); Kevin D. Lance, Troy, MI (US)

(73) Assignee: The Regents of the University of California, Oakland, CA (US)

( * ) Notice: Subject to any disclaimer, the term of this patent is extended or adjusted under 35 U.S.C. 154(b) by 375 days.

(21) Appl. No.: 14/110,549

(22) PCT Filed: Apr. 12, 2012

(86) PCT No.: PCT/US2012/033366
§ 371 (c)(1),
(2), (4) Date: Dec. 19, 2013

(87) PCT Pub. No.: WO2012/142318
PCT Pub. Date: Oct. 18, 2012

(65) Prior Publication Data
US 2014/0170204 A1 Jun. 19, 2014

Related U.S. Application Data

(60) Provisional application No. 61/475,373, filed on Apr. 14, 2011.

(51) Int. Cl.
| | |
|---|---|
| A61F 9/00 | (2006.01) |
| A61K 9/70 | (2006.01) |
| A61K 9/00 | (2006.01) |
| A61K 47/34 | (2017.01) |
| B82Y 30/00 | (2011.01) |
| C08J 5/18 | (2006.01) |
| A61K 47/42 | (2017.01) |
| A61K 31/436 | (2006.01) |
| B82Y 40/00 | (2011.01) |
| A61K 9/20 | (2006.01) |

(52) U.S. Cl.
CPC .......... *A61K 9/0048* (2013.01); *A61F 9/0017* (2013.01); *A61K 9/0051* (2013.01); *A61K 9/7007* (2013.01); *A61K 31/436* (2013.01); *A61K 47/34* (2013.01); *A61K 47/42* (2013.01); *B82Y 30/00* (2013.01); *B82Y 40/00* (2013.01); *C08J 5/18* (2013.01); *A61K 9/2086* (2013.01); *C08J 2300/16* (2013.01); *C08J 2367/04* (2013.01); *C08J 2489/06* (2013.01)

(58) Field of Classification Search
None
See application file for complete search history.

(56) References Cited

U.S. PATENT DOCUMENTS

| | | | |
|---|---|---|---|
| 3,641,237 A * | 2/1972 | Gould | 424/427 |
| 3,961,628 A * | 6/1976 | Arnold | A61F 9/0017 424/427 |
| 6,096,070 A | 8/2000 | Ragheb et al. | |
| 2003/0118649 A1 | 6/2003 | Gao et al. | |
| 2003/0118651 A1* | 6/2003 | Jampani | A61K 9/0024 424/473 |
| 2005/0226826 A1* | 10/2005 | Eason et al. | 424/60 |
| 2006/0269475 A1* | 11/2006 | Ryu | A61K 51/1282 424/1.11 |
| 2007/0134305 A1 | 7/2007 | Zilberman | |
| 2007/0243216 A1* | 10/2007 | Kepka et al. | 424/400 |
| 2008/0128315 A1* | 6/2008 | Buevich et al. | 206/572 |
| 2008/0220039 A1 | 9/2008 | Sherman | |
| 2009/0098183 A1 | 4/2009 | Detamore et al. | |
| 2009/0263430 A1* | 10/2009 | Scheibel et al. | 424/400 |
| 2010/0280452 A1 | 11/2010 | Chen et al. | |
| 2012/0027833 A1 | 2/2012 | Zilberman | |

FOREIGN PATENT DOCUMENTS

| | | |
|---|---|---|
| JP | 201286015 | 5/2012 |
| WO | 2006/002366 | 1/2006 |
| WO | 2006/014484 | 2/2006 |
| WO | 2006/023261 | 3/2006 |
| WO | 2006/110487 | 10/2006 |
| WO | 2007/126411 | 11/2007 |

(Continued)

OTHER PUBLICATIONS

Yan, Wei et al. "Towards nanoporous polymer thin film-based drug delivery systems" Thin Solid Films 517 (2009) 1794-1798.*

(Continued)

*Primary Examiner* — Nicole P Babson
(74) *Attorney, Agent, or Firm* — Bozicevic, Field & Francis LLP; Edward J. Baba; Shweta Chandra

(57) ABSTRACT

Multilayer thin film devices that include a bioactive agent for elution to the surrounding tissue upon administration to a subject are provided. The multilayer thin film devices are useful as medical devices, such as ocular devices. Also provided are methods and kits for localized delivery of a bioactive agent to a tissue of a subject, and methods of preparing the subject devices. The multilayer thin film medical device includes a first layer, a bioactive agent and a second layer. The first and the second layers may be porous or non-porous. The devices have a furled structure, suitable for administration to a subject.

33 Claims, 17 Drawing Sheets

(56) References Cited

FOREIGN PATENT DOCUMENTS

WO    2012/166934    12/2012

OTHER PUBLICATIONS

Addy M, Rawle L, Handley R, Newman HN, Coventry JF. "The development and in vitro evaluation of acrylic strips and dialysis tubing for local drug delivery." J Periodontol. Nov. 1982;53(11):693-9.*

Colin G. Pitt, Margit M. Gratzl, A.Robert Jeffcoat, Ruth Zweidinger, Anton Schindler, Sustained Drug Delivery Systems II: Factors Affecting Release Rates from Poly($\varepsilon$-caprolactone) and Related Biodegradable Polyesters, in Journal of Pharmaceutical Sciences, vol. 68, Issue 12, 1979. pp. 1534-1538 (Year: 1979).*

Cuddon. ("Pharmaceutical Freeze Drying" <https://www.cuddonfreezedry.com/pharmaceutical-freeze-dryng/> available Nov. 7, 2010; accessed Dec. 21, 2017) (Year: 2010).*

Beeley et al., "Fabrication, implantation, elution, and retrieval of a steroid-loaded polycaprolactone subretinal device," J. Biomed. Mater. Res. A 73( 4):437-444 (2005).

Giavaresi et al., "New polymers for drug delivery systems in orthopaedics: in vivo biocompatibility evaluation," Biomedicine & Pharmacotherapy 58(8):411-417 (2004).

Steedman et al., "Enhanced differentiation of retinal progenitor cells using microfabricated topographical cues," Biomedical Microdevices 12(3):363-369 (2010).

Sun et al., "The in vivo degradation, absorption and excretion of PCL-based device," Biomaterials 27(9):1735-1740 (2006).

\* cited by examiner

MULTILAYER THIN FILM DRUG DELIVERY DEVICE AND METHODS OF MAKING AND USING THE SAME

CROSS-REFERENCE TO EARLIER FILED APPLICATION

Pursuant to 35 U.S.C. § 119(e), this application claims priority to U.S. Provisional Patent Application Ser. No. 61/475,373, filed Apr. 14, 2011, which application is incorporated herein by reference in its entirety.

BACKGROUND

Chronic diseases often require long-term treatment strategies that rely on conventional drug delivery methods such as injections and other procedures that necessitate regular hospital or office visits. Controlled long-term drug delivery has many advantages over these traditional methods. Maintaining drug concentration within a clinically relevant therapeutic window minimizes overdosing and drug waste and leads to fewer side effects and an increase in patient compliance and drug efficacy. Several technologies have been developed that utilize these principles of long-term drug delivery, including implantable infusion pumps for the delivery of chemotherapeutics, insulin pumps for the treatment of diabetes mellitus, and spinal drug administration systems for the treatment of lower back pain.

Recent developments in long-term drug delivery systems have included miniaturization to target specific organs. For example, the eye is of interest for long-term controlled drug delivery due to its small size and the chronic nature of many of the diseases that affect it including uveitis, diabetic retinopathy, macular edema, glaucoma, and age-related macular degeneration (AMD).

Protein therapeutics are an effective treatment for many diseases. For example, neovascular AMD is effectively treated with anti-vascular endothelial growth factor (VEGF) formulations such as ranibizumab (Lucentis, Genentech, Inc.) and bevacizumab (Avastin, Genentech, Inc.). These treatments are injected directly into the vitreous cavity on a monthly basis, an invasive procedure whose side effects can include endophthalmitis, intraocular pressure elevation, cataract, and retinal detachment. For AMD specifically, the poor biostability of anti-VEGF drugs and other large protein and antibody-based agents constrains long-term drug delivery. With a half-life of several days, these anti-VEGF drugs clear from the eye after standard intravitreal injection, necessitating monthly super-threshold bolus doses in attempt to prolong therapeutically effective periods.

A sustained and controlled release drug delivery device capable of delivering drugs including protein therapeutics to the anterior and/or posterior segments of the eye while minimizing the number of intraocular injections required for treatment and maintaining a therapeutic concentration of drug within the eye is of interest.

SUMMARY

Multilayer thin film medical devices that include a bioactive agent for elution to the surrounding tissue upon administration to a subject are provided. Also provided are methods and kits for localized delivery of a bioactive agent to a tissue of a subject, and methods of preparing the subject devices. The multilayer thin film medical device includes a first layer, a bioactive agent and a second layer. The first and the second layers may be porous or non-porous. The devices have a furled structure, suitable for administration to a subject via needle or a catheter.

Multilayer thin film devices that include a bioactive agent for elution to the surrounding tissue upon administration to a subject are provided. The devices are useful as medical devices for drug delivery, including ocular devices for delivery of bioactive proteins and small molecules. Also provided are methods of localized delivery of a bioactive agent to a tissue of a subject, and methods of preparing the subject multilayer thin film medical devices.

In certain embodiments, the multilayer thin film medical devices include a first thin film layer, bioactive agent and a second thin film layer, where the bioactive agent is positioned between the first and second layers. The first layer may include a polymer and a pore forming agent. The second layer may be porous or non-porous. The first and second layers may be biodegradable or non-biodegradable. Following administration to a subject, the pore forming agent dissolves to produce a porous first layer and provides for elution of the bioactive agent (e.g., a protein therapeutic) to the surrounding tissue. In some embodiments, the device further includes a third nanostructured porous layer positioned between the first layer and the reservoir of bioactive agent.

In certain embodiments, the multilayer thin film medical devices include a first non-porous thin film layer, a bioactive agent, and a second non-porous thin film layer, where the bioactive agent is positioned in between the first and second layers.

In certain embodiments, the device has a furled structure, where the structure unfurls in vivo in the presence of a hydrating liquid. In certain cases, the device having a furled structure may be administered to a subject by injection into a target tissue.

These devices and methods find use in a variety of applications in which delivery of bioactive agents to subjects is desired.

BRIEF DESCRIPTION OF THE DRAWINGS

The embodiments described in this disclosure are best understood from the following detailed description when read in conjunction with the accompanying to drawings. It is emphasized that, according to common practice, the various features of the drawings are not to-scale. On the contrary, the dimensions of the various features are arbitrarily expanded or reduced for clarity. Included in the drawings are the following figures:

FIGS. 9A-C show a schematic of an exemplary multilayer thin film device (A) and side-profile SEM images of microporous (B) and nanoporous thin film layers (C). FIG. 9D shows a schematic of a multilayer thin film device which includes a centrally located layer including a reservoir in which a bioactive agent is present. The bioactive agent in the reservoir can elute via the nanoporous thin film layers sandwiching the reservoir containing layer. Each of the nanoporous layers are covered by a microporous layer. FIG. 9E provides a schematic of a multilayer thin film device which includes a central layer comprising reservoirs in which two different bioactive agents are present. The bioactive agents in the reservoirs can elute via the nanoporous thin film layers sandwiching the reservoirs containing layer. Each of the nanoporous layers are covered by a microporous layer. FIG. 9F illustrates a multilayer thin film device similar to the one depicted in FIG. 9A with the addition of another reservoir containing the bioactive agent. The two reservoirs include different bioactive reagents (FIG. 9G).

DETAILED DESCRIPTION

Figure 1:
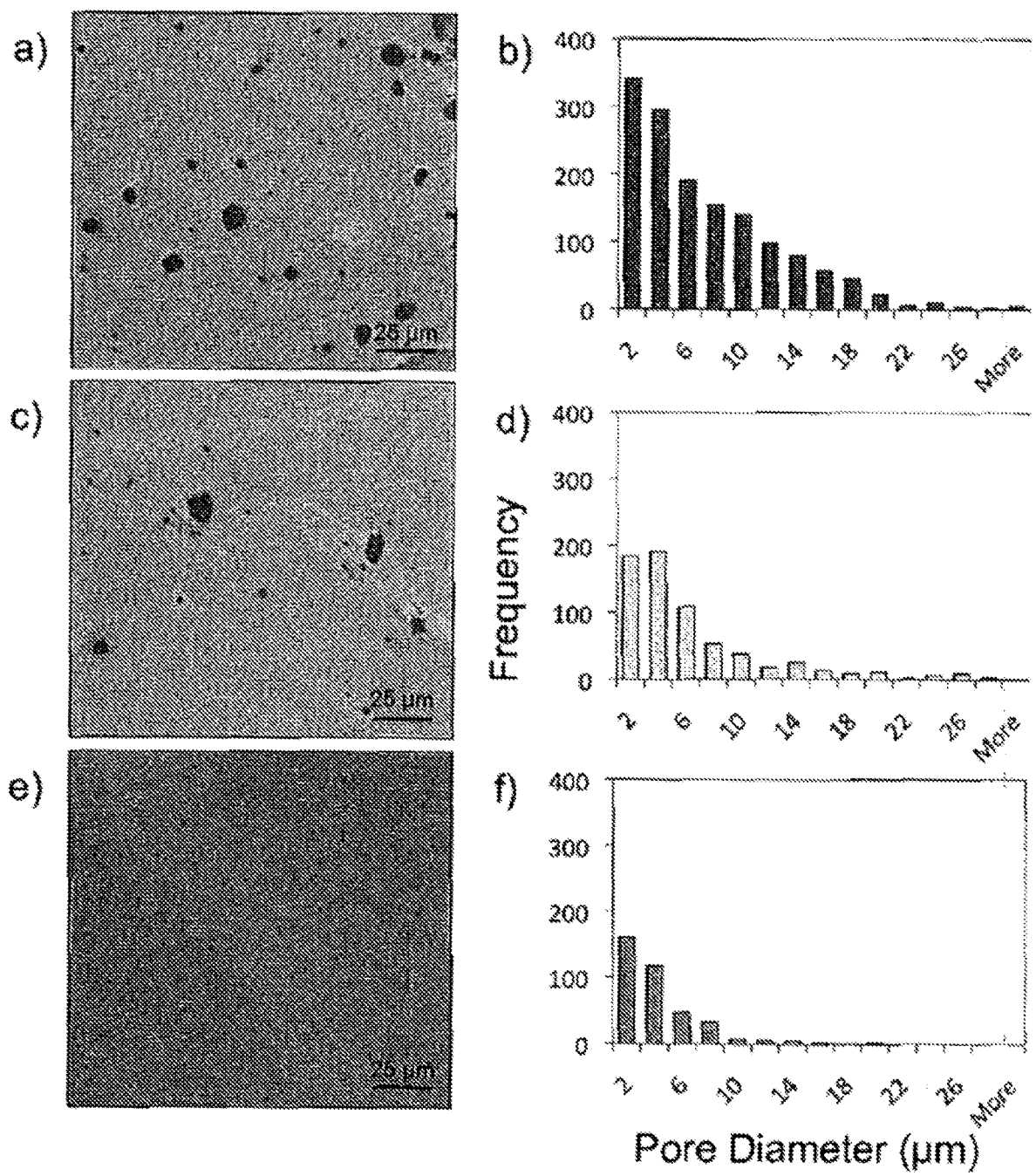
FIGS. 1A-F show scanning electron micrograph (SEM) images and corresponding pore size histograms of polycaprolactone (PCL)/gelatin thin films after five days incubation in PBS.

As summarized above, multilayer thin films that include a bioactive agent for elution to the surrounding tissue upon administration to a subject are provided. The subject devices include a first layer, a bioactive agent and a second layer, where the bioactive agent is positioned between the first and second layers. One or more bioactive agents may be included between the first layer and the second layer. The first and second layers may be non-porous. The first layer may include a biodegradable polymer and a pore forming agent. Following administration to a subject, the pore forming agent dissolves to produce a porous first layer and provides for elution of the bioactive agent (e.g., a protein therapeutic) to the surrounding tissue. In the absence of a pore forming agent the first layer may be non-porous. The second layer may be non-porous or porous. In some embodiments, any or all layers may be non-biodegradable. In other embodiments, the first layer and/or second layer may be biodegradable.

In some embodiments, the device further includes a third nanostructured porous layer positioned between the first layer and the bioactive agent. In certain embodiments, the subject device has a furled structure. The furled structure is suitable for administration of the device to a subject by injection or via a catheter. Once placed into a subject, the structure unfurls in vivo in the presence of a hydrating liquid, which hydrating liquid may be a body fluid of the subject. In some embodiments, the device contains two non-porous films, which are either biodegradable or non-biodegradable with the bioactive agent positioned between these films.

The subject devices contain a reservoir of the bioactive agent for local delivery to the surrounding tissue after placement of the device in a subject. In some embodiments, the bioactive agent is eluted from the device over an extended period of time. Moreover, the release or elution of the drugs or biological agents from the subject devices can be controlled by parameters, such as but not limited to, the size, porosity, thickness, and composition of the thin film layers. The release kinetics of specific drugs is controlled to achieve sustained and substantially constant release of the drug over an extended period of time. Exemplary medical devices for the subject device include, but are not limited to, a cardiovascular device, a neurological device, a neurovascular device, a gastrointestinal device, a muscular device, an ocular device, and the like. In some embodiments, the multilayer thin film can be used for localized delivery of the bioactive agent to a soft tissue, such as joint space, nerve, liver, kidney, gastrointestinal tract, pancreas, prostate, colon, and the like.

In some embodiments, the device contains more than one reservoir positioned between the first and second film layer, where each reservoir contains a single bioactive agent or two or more different bioactive agents. The subject device may be injected into a target tissue, or surgically implanted in a target tissue, or administered orally.

Before certain embodiments are described in greater detail, it is to be understood that this disclosure is not limited to the certain embodiments described, as such may, of course, vary. It is also to be understood that the terminology used herein is for the purpose of describing particular embodiments only, and is not intended to be limiting, since the scope of the disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the embodiments described herein, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Multilayer Thin Films

Multilayer thin film medical devices that include a plurality of thin film layers and a bioactive agent for use in the local delivery of the bioactive agent to a tissue of a subject in need thereof are provided. In some embodiments, at least one thin film, such as 1, 2, 3, 4, 5 or more thin films, of the subject device includes a biodegradable or non-degradable polymer and a pore forming agent. In some embodiments, at least one thin film, such as 1, 2, 3, 4, 5 or more thin films, of the subject device is a porous thin film (e.g., a microporous thin film or a nanoporous thin film). In some embodiments, the plurality of thin film layers are non-porous and include a bioactive agent between two non-porous thin film layers.

In some embodiments, a multilayer thin film medical device includes a first layer including a biodegradable or non-degradable polymer and a pore forming agent, a bioactive agent, and a second layer in contact with the bioactive agent, where the bioactive agent is positioned between the first layer and the second layer.

In some embodiments, the second layer is a non-porous layer (e.g., a backing layer). In some embodiments, the second layer is a porous layer (e.g., a microporous or nanoporous layer). The second layer may include a biodegradable or non-degradable polymer and a pore forming agent. In certain embodiments, the second layer is a nanostructured porous layer.

In some embodiments, the multilayer thin film medical device includes a bioactive agent that is positioned between two porous layers. In some cases, one or both of the layers is a nanostructured porous layer. In some cases, one or both of the layers is a microporous layer. In some embodiments, the multilayer thin film medical device includes a reservoir of a bioactive agent that is positioned between two layers, where one or both of the layers includes a biodegradable or non-degradable polymer and a pore forming agent. In certain embodiments, the subject device further includes one or more additional nanostructured porous layers positioned between the first and/or second layer and the reservoir of the bioactive agent.

In some embodiments, a multilayer thin film medical device includes a first layer including a biodegradable or non-degradable polymer and a pore forming agent, a bioactive agent, and a second non-porous layer in contact with the bioactive agent, where the bioactive agent is positioned between the first layer and the second layer.

In some embodiments, a multilayer thin film medical device includes a first porous layer including a biodegradable or non-degradable polymer, a bioactive agent, and a second non-porous layer in contact with the bioactive agent, where the bioactive agent is positioned between the first layer and the second layer.

In certain embodiments, the subject device includes a furled structure (e.g. a substantially cylindrical, substantially conical, or substantially frusto-conical structure). In certain embodiments, the subject device includes an unfurled structure, where the structure may have a substantially circular peripheral edge.

In certain embodiments, the subject device further includes a third nanostructured porous layer positioned between the first layer and the reservoir of the bioactive agent.

In some embodiments, a multilayer thin film medical device includes a first non-porous layer including a biodegradable or non-degradable polymer, a bioactive agent, and a second non-porous layer in contact with the bioactive agent, where the bioactive agent is positioned between the first layer and the second layer.

In certain embodiments, in the subject devices, the first non-porous layer and the second non-porous layer are in contact with each other at the edges of the multilayer thin film thereby sealing the bioactive drug inside the multilayer thin film. In certain embodiments, either or both of the non-porous layers are biodegradable. In other embodiments, the either or both of the non-porous layers are non-biodegradable.

In certain embodiments, in the subject devices, the bioactive agent is present as a thin pellet of lyophilized material. In certain embodiments, in the subject devices, the bioactive agent is deposited in a plurality of reservoirs are located across one surface of the second non-porous layer. In other embodiments, two or more bioactive agents are deposited in the plurality of reservoirs, for example, in the same reservoir or in different reservoirs.

In certain embodiments, a first bioactive agent is deposited in a first reservoir of the plurality of reservoirs located across one surface of the second non-porous layer and a second bioactive agent is deposited in a second reservoir of the plurality of reservoirs.

In other embodiments, a plurality of bioactive agents is present in the multilayer thin film device. For example, two or more bioactive agents may be present in between a first thin film layer and a second thin film layer.

Pore Forming Agents

The pore forming agent is capable of dissolving or eroding away from the first thin film layer to produce a porous first thin film of the polymer that remains. Application of suitable conditions, e.g., contact with an aqueous liquid in vivo, will dissolve the pore forming agent. Exemplary conditions are set forth below. For example, upon placement of the device in the eye of a subject, the pore forming agent is contacted with vitreous fluid and dissolves away thereby providing release over time of the bioactive agent through the pores that are formed in the thin film. In certain embodiments, the dissolution of the pore forming agent is rapid, e.g., elution of the bioactive agent begins within about 60 minutes after administration, such as within about 30 minutes, within about 15 minutes, within about 10 minutes, within about 5 minutes, or within about 2 minutes after administration.

In some embodiments, the porous thin film that is formed after dissolution of the pore forming agent is microporous, e.g., the thin film comprises a porous structure having pore sizes of about 1 µm to about 100 µm, such as about 1 µm to about 30 µm, about 1 µm to about 20 µm, or about 1 µm to about 10 µm. In certain embodiments, the porous thin film has an average pore size of between about 1 µm and about 30 µm, such as between about 1 µm and about 15 µm, between about 1 µm and about 10 µm, or between about 1 µm and about 5 µm. In certain embodiments, the porous thin film has a % porosity of between about 20% and about 0.01%, such as between about 10% and about 0.1%, between about 5% and about 0.1%, or between about 2% and about 0.1%, and including between about 0.1% and about 0.4%, between about 0.4% and about 1%, and between about 1% and about 2%. In certain embodiments, the microporous thin film has % porosity of 0.1%, 0.5% or 1.8%.

In some cases, the pore forming agent is biocompatible and/or biodegradable, and capable of dissolution upon administration to a subject. A suitable pore forming agent may be selected in view of the specific bioactive agent and composition of the thin films, and the desired elution profile or release rate. Any suitable water soluble polymer or hydrogel may be used as a pore forming agent. The pore forming agent may be a naturally occurring agent or polymer or a synthetic agent or polymer. In some embodiments, the pore forming agent is a water soluble polymer such as a polyethylene glycol, a polyoxyethylene copolymer, an acrylate polymer, an acrylate-acrylic acid copolymer, a polyacrylic acid, an acrylate copolymer including quaternary ammonium groups, a polyacrylamide, a polyvinyl alcohol, hyaluronan, or a polyvinylpyrrolidone.

In some embodiments, the pore forming agent is a carbohydrate, a protein or protein derivative, or the like. Exemplary pore forming reagents include, but are not limited to, gelatin, a polyethylene glycol (PEG), chitosan, polyvinylpyrrolidone (PVP), polyvinyl alcohol, or agarose. Any suitable PEG may be selected as a pore forming agent.

In certain embodiments, at least one thin film of the subject devices includes a ratio by mass of biodegradable or non-biodegradable polymer to pore forming agent that is in the range of between about 1:2 and 99:1, such as between about 1:2, 1:5, or about 7:3 and 9:1, such as about 7:3, about 8:2 or about 9:1.

Biodegradable Polymers

In some embodiments, the subject devices are biodegradable. In some embodiments, the plurality of thin films of the subject devices each independently include a biodegradable polymer. In some embodiments, the second non-porous thin film layer includes a biodegradable polymer. In some embodiments, the one or more nanoporous thin film layer includes a biodegradable polymer. Thin films of the subject devices can be fabricated from a variety of suitable materials. Exemplary biodegradable polymers include, but are not limited to, biodegradable or bioerodible polymers, such as poly(DL-lactide-co-glycolide) (PLGA), poly(DL-lactide-co-ε-caprolactone) (DLPLCL), poly(ε-caprolactone) (PCL), or combinations or copolymers thereof, as well as natural biodegradable polymers, such as collagen, and the like. PLGA is a bulk-eroding copolymer of polylactide (PLA) and polyglycolide (PGA). In some embodiments, the biodegradable polymer includes PLA, PGA, PCL, PLGA, or PLCL.

In some embodiments, the biodegradable polymer includes polycaprolactone (PCL). PCL is an exemplary polymer that is biocompatible and biodegradable in vivo and well tolerated throughout the duration of the presence and degradation of the device, [see e.g., Sun et al., "The in vivo degradation, absorption and excretion of PCL-based device." Biomaterials 27(9) (2006) 1735-1740; Beeley et al., "Fabrication, implantation, elution, and retrieval of a steroid-loaded polycaprolactone subretinal device." J. Biomed. Mater. Res. A, 73(4) (2005) 437-444; Giavaresi et al., "New polymers for drug delivery systems in orthopaedics: in vivo biocompatibility evaluation. Biomedicine & Pharmacotherapy 58(8) (2004) 411-417].

In some cases, under physiological conditions the biodegradable polymer degrades by random chain scission, which gives rise to a two-phase degradation. Initially, as molecular weight decreases the physical structure is not significantly affected. Degradation takes place throughout the polymer material, and proceeds until a critical molecular weight is reached, when degradation products become small enough to be solubilized. At this point, the structure starts to become significantly more porous and hydrated. For example, one combination of fast-resorbing PGA and slow-resorbing PLA allows PLGA copolymers to have a resorption rate of approximately 6 weeks.

In some cases, the biodegradable polymer has a MW of about 80 kDa or more and does not degrade until after 1 year or more in the tissue of a subject. In some embodiments, the macroscopic degradation of a biodegradable polymer (e.g., PCL) may occur at about 8 kDa. In some embodiments, the MW of the biodegradable polymer is selected so as to tune the degradation time of the material in vivo. For example, a PCL polymer of about 15 to about 20 kDa may start to structurally break down after 4 months and lose mechanical integrity by 6 months.

In some embodiments, the biodegradable polymer includes a polymer having a MW of about 10 kDa or more, such as about 15 kDa or more, about 20 kDa or more, about 30 kDa or more, about 40 kDa or more, about 50 kDa or more, about 60 kDa or more, about 70 kDa or more, about 80 kDa or more, about 90 kDa or more, or about 100 kDa or more. In some embodiments, the biodegradable polymer includes a blend of polymers where the polymers may be of the same or a different type of polymer, and each polymer may be of a different MW. In some embodiments, the biodegradable polymer includes a blend of a high MW polymer and a low MW polymer. The high MW polymer may be of about 25 kDa or more, such as about 30 kDa or more, about 40 kDa or more, about 50 kDa or more, about 60 kDa or more, about 70 kDa or more, about 80 kDa or more, about 90 kDa or more, or about 100 kDa or more. The low MW polymer may be of about 20 kDa or less, such as about 15 kDa or less, about 10 kDa or less, about 8 kDa or less, about 6 kDa or less, or about 4 kDa or less.

In some embodiments, the ratio by mass of the high MW polymer to the low MW polymer in a blend of polymers is between about 1:9 and about 9:1, such as between about 2:8 and about 8:2, between about 2:8 and about 6:4, or between about 2:8 and about 1:1. In certain embodiments, the ratio by mass of the high MW polymer to the low MW polymer is about 3:17, about 2:8, about 1:3, about 3:7, about 7:13, about 2:3, about 9:11, about 1:1, about 11:9, or about 3:2. In some embodiments, the composition of the biodegradable polymer is selected to provide a melting temperature ($T_m$) of between about 50° C. and about 70° C., such as between about 58° C. and about 63° C. In some embodiments, the composition of the biodegradable polymer is selected to provide a glass transition ($T_g$) of between about −50° C. and about −80° C., such as between about −60° C. to about −65° C.

In some embodiments, the thickness of the biodegradable polymer layer may range from about 1 micron to about 100 microns. In some embodiments, the thickness of the biodegradable polymer layer may range from about 100 nm to about 990 nm. For example, the thickness of the biodegradable polymer layer may be about 100 nm, 200 nm, 300 nm, 400 nm, 500 nm, 600 nm, 700 nm, 800 nm, 900 nm, or 990 nm.

Reservoir of Bioactive Agent

The subject devices include a reservoir of one or more biological agents. The reservoir is contained within the subject device, such that upon administration, the bioactive agent is subsequently eluted from the device into the surrounding tissue of the subject through one or more porous thin film layer.

In some embodiments, the subject device utilizes a bioactive agent in a dry lyophilized form, packaged within the device and subsequently resolubilized in situ for release into the surrounding tissue following administration. For example, after insertion into the eye, lyophilized bioactive agent is sequestered within the device, restricted from the ocular environment within the reservoir, maintaining bioactivity for months, where rehydration and release are controlled via engineered pores (e.g., in a nanoporous thin film and/or a microporous thin film). In such embodiments, the stability and bioactivity of bioactive agent in the reservoir is maintained for an extended period of time after administration.

Figure 3:
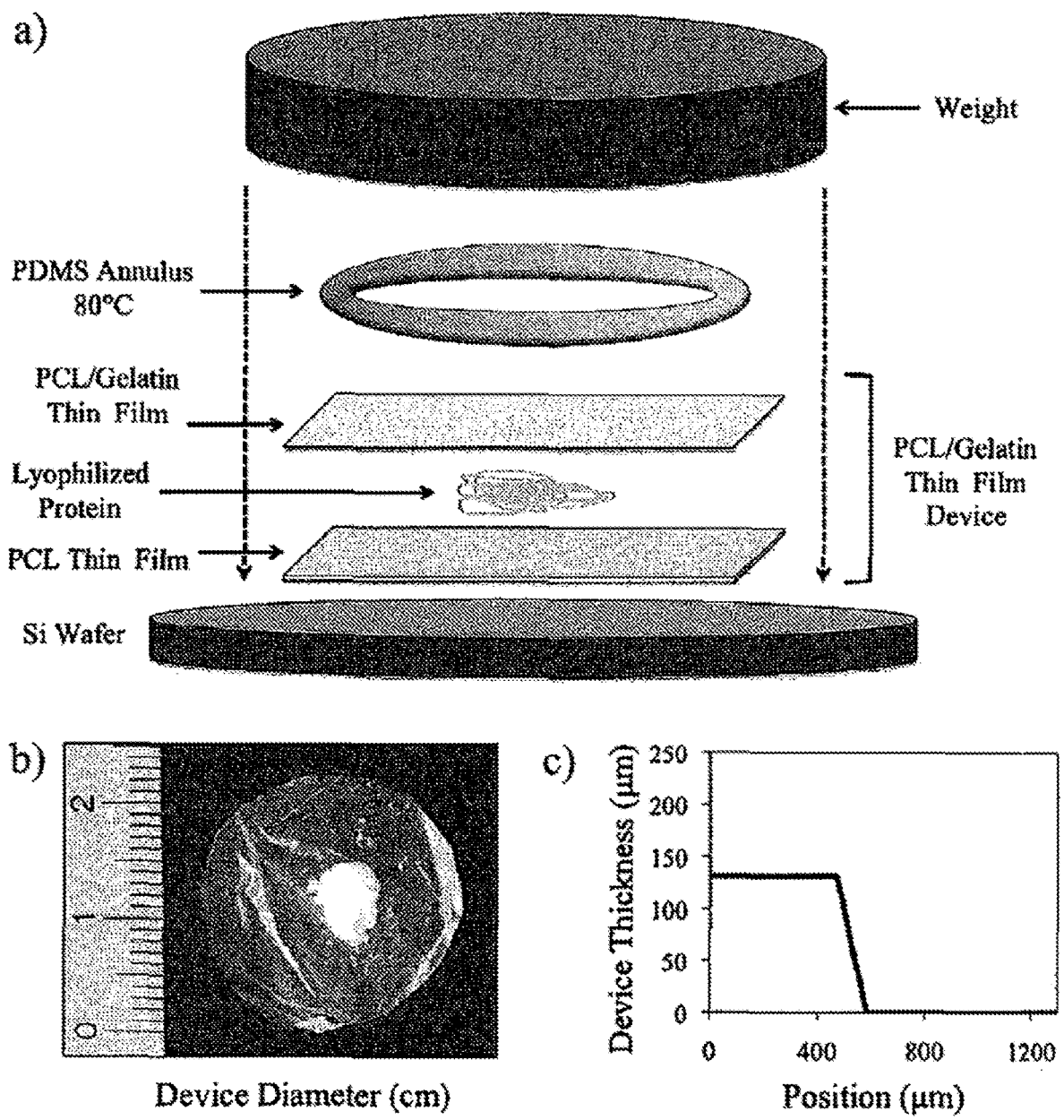
FIGS. 3A-C illustrate the fabrication of a multilayer thin film device. (A) Fabrication; (B) a finished device of ~2 mm in diameter; and (C) profile of the device edge.

In some embodiments, the reservoir is defined by a continuous layer of a composition that includes the bioactive agent. For example, a layer of lyophilized material as depicted in FIG. 3. In such embodiments, the reservoir of bioactive agent is positioned between a first thin film layer, and a second thin film (e.g., a non-porous thin film), where the first layer may be a thin film that includes a biodegradable or non-biodegradable polymer and a pore forming agent, or a microporous thin film from which the pore forming agent has dissolved. In certain embodiments, a third nanoporous thin film layer is positioned between the first layer and the reservoir of bioactive agent.

Figure 10:
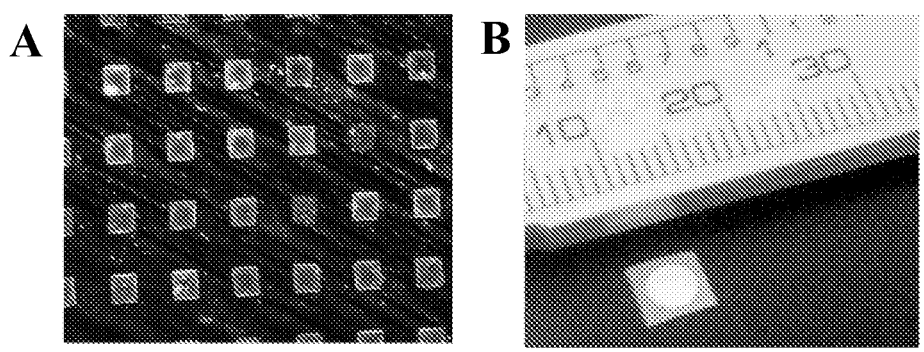
FIG. 10A shows wells in a non-porous PCL thin film that are filled with FITC-IgG protein.
FIG. 10B shows the dimensions of an exemplary multilayer thin film device.

In some embodiments, the reservoir is defined by a plurality of structures in a thin film layer, such as but not limited to, wells, pores, chambers or channels located through and/or across a surface of the thin film, where the structural voids are filled with a composition that includes the bioactive agent. For example, the reservoir may be defined by a plurality of wells in a non-porous thin film that are filled with bioactive agent, as depicted in FIG. 10. In such embodiments, the reservoir defined by the plurality of structures may be covered with a further thin film that provides a porous layer upon administration through which the bioactive agent can diffuse (e.g., a nanoporous thin film, a microporous thin film or precursor thereof, or a combination thereof). In such cases, this reservoir defined by the plurality of structures may be described as being positioned between a first thin film layer and a second thin film layer. In some cases, the reservoirs may include a plurality of bioactive agents. In some embodiments, a first reservoir of the plurality of reservoirs may include a first bioactive agent, a second reservoir of the plurality of reservoirs may include a second bioactive agent. In some embodiments, a plurality of different bioactive agents may be present in the different reservoirs. In some embodiments, the reservoir is defined by multiple thin film layers (e.g., multiple layers of about 10 μm or less in thickness) where each layer may sequester bioactive drug, and where each layer may be protected from exposure to a hydrating liquid (e.g., liquid from the surrounding tissues of a subject) by the layer above it. In such cases, after administration, bioactive drug is eluted successively from each layer of the reservoir over an extended period of time. Each layer of the reservoir may further comprise a biodegradable polymer that includes structures, such as nanostructures of pores, channels or wells.

The pore forming agent may protect the bioactive agent from degradation by sealing and maintaining the bioactive agent in the device in a lyophilized state. In certain embodiments, the device is storage stable, e.g., the bioactive agent is a protein therapeutic that maintains its bioactivity for an extended period of time, such as, 1 or more months, 2 or more, 3 or more, 6 or more, 9 or more or 12 or more months. In some embodiments, dissolution of the pore forming agent provides for an elution profile of the bioactive agent to the surrounding tissue upon placement of the device in a subject (e.g., a delayed elution profile, two elution profiles, a substantially zero order elution profile).

Exemplary bioactive agent include, but are not limited to, polypeptides, nucleic acids, such as DNA, RNA, and siRNA, growth factors, steroid agents, antibody therapies, antimicrobial agents, antibiotics, antiretroviral drugs, anti-inflammatory compounds, antitumor agents, anti-angiogeneic agents, and chemotherapeutic agents. In certain embodiments, the multilayer thin film includes a covalently attached bioactive agent. In some embodiments, the multilayer thin film device further includes cells, such as stem cells, pancreatic islets or beta cells, retinal progenitor cells, cardiac progenitor cells, osteoprogenitor cells, neuronal progenitor cells, and the like.

Any convenient bioactive agent may be selected for use in the subject devices. In some embodiments, the bioactive agent is a small molecule or a large molecule, such as a protein (e.g., a protein biologic or an antibody) or an aptamer (e.g., a single stranded polynucleotide drug). In certain cases, the bioactive agent may be combined with a pharmaceutically acceptable additive before or after placement of the bioactive agent on a layer of the subject device. The term "pharmaceutically acceptable additive" refers to preservatives, antioxidants, emulsifiers, dyes and excipients known or used in the field of drug formulation and that do not unduly interfere with the effectiveness of the biological activity of the active agent, and that is sufficiently non-toxic to the patient. For example, the bioactive agent may be formulated with inert fillers, anti-irritants, gelling agents, stabilizers, surfactant, emollients, coloring agents, preservatives, or buffering agents, as are known in the art. The term "excipients" is conventionally known to mean carriers, diluents and/or vehicles used in formulating drug compositions effective for the desired use.

In some embodiments, the bioactive agent is a small molecule, such as but not limited to, an anti-glaucoma drug, an anti-inflammatory drug, an immunosuppressant drug, a vitamin, micronutrient or antioxidant, an antibacterial drug (e.g., vancomycin or cephazolin), an anti-viral drug (e.g., gancyclovir, acyclovir or foscarnet), an anti-fungal drug (e.g., amphotericin B, fluconazole or voriconazole) or an anti-cancer drug (e.g., cyclophosphamide or melphalan). In certain embodiments, the small molecule is a vitamin, micronutrient or antioxidant, such as but not limited to, vitamin A, vitamin C, vitamin E, zinc, copper, lutein or zeaxanthin. In certain embodiments, the small molecule is an immunosuppressant drug, such as but not limited to, cyclosporine, methotrexate or azathioprine. In certain embodiments, the small molecule is an anti-inflammatory drug, such as but not limited to, a corticosteroid (e.g., triamcinolone acetonide or dexamethasone) or a non-steroidal drug (e.g., ketorolac or diclofenac). In certain embodiments, the small molecule drug is an anti-glaucoma drug, such as but not limited to, latanaprost, travarost, timolol, brimonidine or dorzolamide.

In certain embodiments, the small molecule may be a hydrophobic small molecule. In other embodiments, the small molecule may be a hydrophilic small molecule. In general, small molecules do not include proteins.

In some embodiments, the bioactive agent is a large molecule drug that is an anti-angiogenic drug, an anti-VEGF drug, an immunosuppressant drug, a complement inhibitor, a neuromuscular blocker drug, a hematopoietic factor (e.g., erythropoietin), a thrombolytic drug (e.g., tissue plasminogen activator) or a collagenolytic drug (e.g., hyaluronidase or microplasmin) In certain embodiments, the large molecule drug is an immunosuppressant drug, such as but not limited to, etanercept, infliximab or daclizumab. In certain embodiments, the large molecule drug is a neuromuscular blocker drug, such as but not limited to, botulinum toxin A. In certain embodiments, the large molecule drug is a complement inhibitor, such as but not limited to, an anti-C3 compound.

In some embodiments, the bioactive agent is a protein, such as but not limited to, an antibody therapeutic, such as ranibizumab (Lucentis©, Genentech, Inc.), bevacizumab (Avastin®, Genentech/Roche), trastuzumab (Herceptin®, Genentech, Inc.), rituximab (Rituxan®, Genentech, Inc.), gentuzumab ozogamicin (Myllotarg®, Pfizer, Inc.) or cetuximab (Erbitux®, ImClone LLC); an enzyme such as but not limited to, a collagenase, a peptidase, or an oxidase; a protein therapeutic, such as but not limited to, insulin, erythropoietin (e.g., rHuEPO-alpha, Epoetin alfa), a blood factor, an interferon (e.g., interferon alfa-2b (INTRON® A) or peginterferon alfa-2b). In certain embodiments, the bioactive agent is a protein that modulates the activity of a therapeutic target, such as but not limited to, VEGF, GP120, RANKL, NGF or TNF-alpha. In certain embodiments, the bioactive agent is a large molecule drug that is an anti-angiogenic drug (e.g., a PDGF inhibitor or an anti-VEGF drug). In certain embodiments, the bioactive agent is a VEGF antagonist, such as but not limited to ranibizumab or bevacizumab.

In some embodiments, the bioactive agent is a protein therapeutic, such as but not limited to ranibizumab, bevacizumab, trastuzumab, rituximab, gentuzumab ozogamicin or cetuximab.

The bioactive agents may be in a purified form, partially purified form, recombinant form, or any other form appropriate for inclusion in the multilayer thin film medical device. The agents may be free of impurities and contaminants. The bioactive agent(s) disposed in the multilayer thin film medical device may be include stabilizing agents as additives to increase the stability of the bioactive agent(s). For example, the bioactive agent may be combined with a stabilizer, such as commercially available stabilizers. In general, the stabilizer used may depend upon the type of bioactive agent(s) included in the multilayer thin film device.

Nanoporous Thin Films

In some embodiments, one or more thin film layers, such as 1, 2, 3 or more thin films, of the subject devices are nanoporous. As used herein, the term "nanoporous" refers to a nanostructured thin film porous layer where the average pore size is sub-micrometer, such as between about 1 nm and about 990 nm, between about 1 nm and about 100 nm, between about 2 nm and about 700 nm, between about 2 nm and about 500 nm, between about 3 nm and about 400 nm, between about 5 nm and about 200 nm, or between about 7 nm and about 50 nm.

In some embodiments, a nanoporous thin film is positioned between another thin film as described above (e.g., that includes a biodegradable polymer and a pore forming agent), and a reservoir of bioactive agent. The nanoporous thin film is in contact with the bioactive agent and provides for a desired elution profile of the bioactive agent (e.g., a substantially zero-order elution profile that avoids an initial burst effect) from the subject device. For example, by controlling parameters of the nanoporous thin film such as pore size, polymer thickness, porous area, and pore density, the nanoporous thin film can act as a diffusion barrier for a variety of bioactive agents.

In certain embodiments, the average pore size of the nanoporous thin film approaches the size of the bioactive agent solute (e.g., an protein therapeutic), such that the bioactive agent molecules diffuse via single file diffusion (SFD) or hindered diffusion through the nanopores. In such cases, substantial deviations from Fick's laws may occur and diffusion of the bioactive agent may occur independently of the concentration gradient of bioactive agent.

In some embodiments, the nanoporous thin film includes a biodegradable polymer as described above (e.g., PCL). In some embodiments, the nanoporous thin film has a thickness of about 10 μm or less, such as about 8 μm or less, about 6 μm or less, about 4 μm or less, about 2 μm or less, or about 1 μm or less.

Multilayer Thin Film Structures

The subject devices may form any convenient structure, such as but not limited to, a furled or an unfurled structure, a folded structure, a tubular structure, a planar structure, a toric structure or a discoid structure.

In some embodiments, the subject devices form either a furled or an unfurled structure. As used herein, the term "furled" refers to a structure of a material where the material is curled or rolled upon itself (e.g., the structure is an annular sheet disposed about a central axis) as compared to a substantially planar, flat or "unfurled" structure of the material. The term "furling" refers to the process of transforming a material from an unfurled structure to a furled structure (e.g., whereby a flat sheet curls around a central axis to form an annular structure). The term "unfurling" refers to the reverse process where the thin film is unrolled, unfolded, or spread out. Application of suitable furling or unfurling conditions to a subject device can result in transformation to produce a desired to furled or unfurled structure, respectively. A multilayer thin film device structure of the present disclosure may spontaneously furl or unfurl in response to suitable conditions. For example, drying conditions sufficient to furl the subject device and produce a furled structure. Alternatively, contact of a furled multilayer thin film structure with a hydrating liquid (e.g., vitreous fluid present in the eye of a subject), produces a substantially planar unfurled structure. In some cases, upon administration and contact with a hydrating liquid, the multilayer thin film medical device expands. By "expands" is meant that the thin film becomes larger in size or volume as a result of the surrounding liquid hydrating the film.

Figure 7:
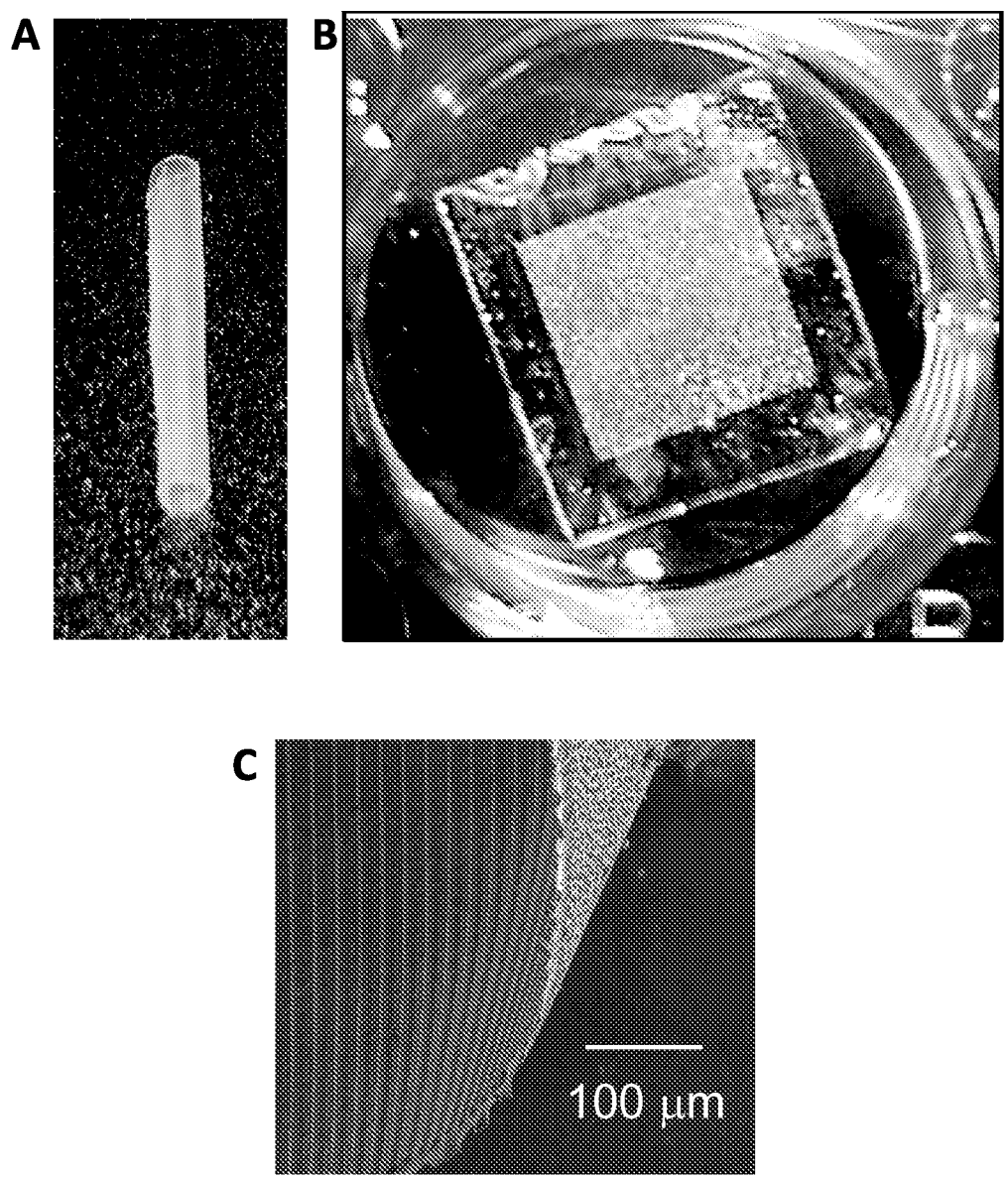
FIGS. 7A-C show a furled thin film device (A), and an unfurled device (B), that has a thin form factor (C).
Figure 8:
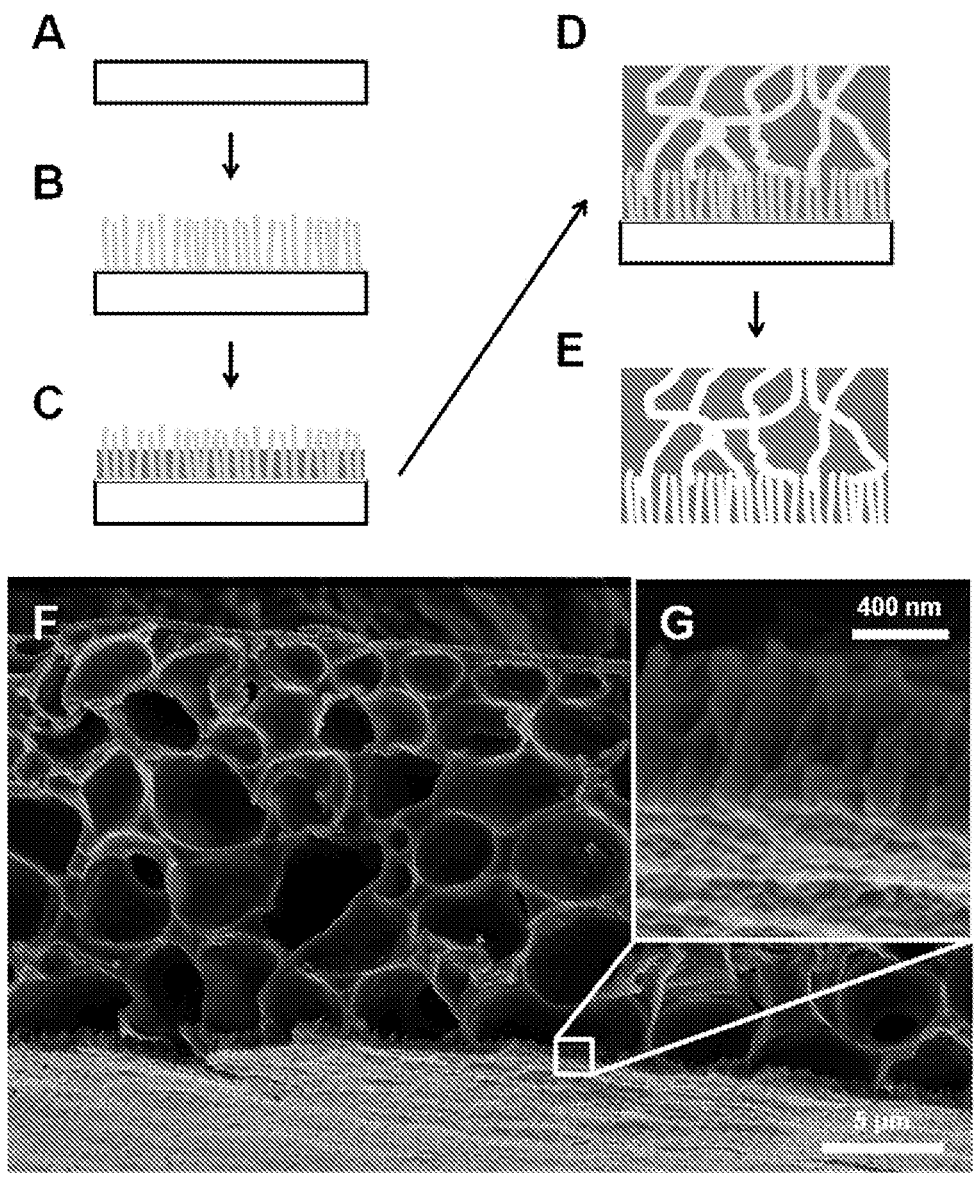
FIGS. 8A-E illustrate thin film fabrication procedure.
FIGS. 8F-G show scanning electron microscope (SEM) images of a typical nanostructured PCL film.

In certain embodiments, the furled structure is substantially cylindrical, e.g., a structure where a planar film has curled upon itself to form a cylindrical shape as depicted in FIG. 7. In certain embodiments, the furled structure is substantially frusto-conical. By frusto-conical is meant a structure having the shape of a frustum of a cone, i.e., the shape of a cone whose tip has been truncated by a plane parallel to its base.

In certain embodiments, the device has an unfurled structure that includes a substantially circular peripheral edge.

In some embodiments, the multilayer thin film devices are fabricated to have a diameter of between about 1 mm and about 50 mm, such as between about 1 mm and about 10 mm, between about 2 mm and about 8 mm, between about 3 mm and about 7 mm, between about 4 mm and about 6 mm. In some cases, the diameter is about 1 mm, about 2 mm, about 3 mm, about 4 mm, about 5 mm, about 6 mm, about 7 mm, about 8 mm, about 9 mm or about 10 mm. In some embodiments, the multilayer thin film devices are fabricated to have an area between about 1 mm$^2$ and about 100 mm$^2$, including between about 4 mm$^2$ and about 64 mm$^2$, between about 9 mm$^2$ and about 49 mm$^2$, between about 16 mm$^2$ and about 36 mm$^2$, such as about 16 mm$^2$, about 25 mm$^2$, or about 36 mm$^2$.

In some embodiments, the multilayer thin film is fabricated to have a thickness between about 1 μm and about 1 mm, such as between about 10 μm and about 500 μm, between about 50 μm and about 300 μm, between about 100 μm and about 200 μm, such as about 100 μm, about 125 μm, about 150 μm, about 175 μm or about 200 μm.

Methods of Preparation

Also provided are methods of preparing the subject multilayer thin film medical devices. In some embodiments, the method includes fabricating a first thin film layer that includes a biodegradable or non-degradable polymer and a pore forming agent; depositing a layer of bioactive agent over the first thin film layer; positioning a second thin film layer (e.g., a non-porous or porous layer) over the layer of bioactive agent to produce a multilayer thin film structure; sealing the bioactive agent between the first thin film layer and the second thin film layer, by using an adhesive, or by using heat, or a solvent to melt the layers; and forming a furled structure of the multilayer thin film device by drying the multilayer thin film structure for a sufficient period of time or by mechanically rolling the device. In some embodiments, a single film may be sealed to itself around a bioactive reservoir to create a single film multilayer device.

The thin film layers may be fabricated using any convenient method. For example, the first thin film layer that includes a biodegradable or non-biodegradable polymer and a pore forming agent, as described above, may be fabricated by spin-casting a solution of biodegradable polymer (e.g., PCL) and pore forming agent (e.g., gelatin) onto a flat circular mold using methods readily adapted from those described by Steedman et al. ("Enhanced differentiation of retinal progenitor cells using microfabricated topographical cues. Biomedical Microdevices", 12(3) (2010) 363-369). The second non-porous thin film layer may be fabricated using similar methods to those described above. Devices with non-porous first thin film layers may be fabricated using similar methods to those described above.

A reservoir of bioactive agent may be prepared in the subject multilayer thin films, e.g., as a discrete layer of a composition that includes the bioactive agent. The layer of bioactive agent may be prepared using any convenient method. For example the bioactive agent may be deposited as a lyophilized composition. For example, the layer of bioactive agent may be formed by application to a thin film of a solution that includes the bioactive agent followed by subsequent drying (e.g., evaporation, lyophilization). The layer of bioactive agent is positioned between the first and second thin film layers.

In certain embodiments, the sealing step of the subject methods is performed using an annulus that may be heated. An exemplary heating step includes the use of an annulus (e.g., a PDMS annulus heated) that is heated to a temperature (e.g., 80° C.) above the melting temperature of the polymers (e.g., PCL) used in the fabrication of the thin film layers. Application of the heated annulus to one surface of the multilayer thin films (e.g., by pressing down on the annulus with a flat stainless steel weight for 30 seconds) melts and seals the films together to produce a multilayer thin film structure having a annular circumference. The size and shape of the annulus may be selected to produce devices of a desired size. In such cases, the first thin film layer and the second thin film layer are bonded thereby sealing the bioactive agent between the multilayer thin film structure.

In certain embodiments, the sealing step of the subject methods is performed using a laser beam to heat a defined area of the thin film layers, for example, a circular area surrounding the area where the bioactive agent has been disposed. In certain embodiments, the sealing step of the subject methods is performed by disposing an adhesive material on one or both of the thin film layers. For example, an adhesive material may be disposed on the first thin film layer and/or the second thin film layer in an area surrounding the area where the bioactive agent is disposed. The adhesive may seal the two layers when the two layers are brought in contact. Alternatively, the adhesive may be a heat sensitive adhesive or a pressure sensitive adhesive. In these embodiments, heat or pressure may be applied in order to seal the layers of the thin film device.

In some embodiments, forming a furled multilayer thin film device may be performed by drying the multilayer thin film device, for example, under conditions sufficient to allow the multilayer thin film structure to form a furled structure. Exemplary drying conditions include lyophilizing conditions under reduced pressure, where most of the water present may be evaporated from the multilayer thin film device while the stability and bioactivity of the bioactive agent is maintained. In other embodiments, forming a furled multilayer thin film device may be performed by mechanically rolling the multilayer thin film device into a furled structure.

In some embodiments, the method of preparing the subject device is a method that includes fabricating a first nanoporous thin film layer over a nanotemplate; fabricating a second thin film layer comprising a biodegradable polymer and a pore forming agent over the first nanoporous thin film layer; removing the first and second thin film layers from the nanotemplate; fabricating a third non-porous thin film layer comprising a plurality of reservoir wells; depositing a bioactive agent in the plurality of reservoir wells; positioning the third non-porous thin film layer over the first and second layers to produce a multilayer thin film structure; sealing the multilayer thin film structure to bond the first thin film layer to the third thin film layer thereby sealing the bioactive agent between the multilayer thin film structure; and furling the multilayer thin film device by, for example, drying the multilayer thin film device for a sufficient period of time to allow the multilayer thin film structure to form a furled structure, or by rolling the multilayer thin film device, such as mechanically rolling.

The subject method may be performed using methods similar to those described above. The first nanoporous thin film layer may be fabricated by any convenient method. For example, a nanotemplate synthesis method may be used to produce nanostructures in a biodegradable polymer thin films that are readily adapted for use in the subject methods of preparation. An inorganic nanotemplate of aligned and ordered nanowires (e.g., ZnO rods) may be prepared using any convenient method. A variety of techniques may be used to deposit a polymer (e.g., a biodegradable polymer) onto the nanotemplate. For example, the polymer can be heated above its melting point and allowed to conform to the template. For example, spin casting of polymer solutions may be used. In some cases, to provide mechanical robustness, prior to template removal, a second thin film layer (e.g., a microporous thin film layer, or a layer that includes a pore forming agent) is fabricated on top of the first nanoporous thin film layer. In some embodiments, the thickness of the nanoporous thin film layer corresponds to the lengths of the nanorods of the template.

A reservoir of one or more bioactive agents may be incorporated into the multilayer thin film before administration to a subject, using any convenient method. For example, by depositing a lyophilized material on a thin film, or by dipping the device during fabrication into a solution or dispersion containing the agent. In some embodiments, a composition that includes the bioactive agent is deposited on a thin film that includes a plurality of structures, as described above. The composition fills the structural voids defined by these structures (e.g., wells across on surface of a nonporous thin film as depicted in FIG. 10A). The reservoir of bioactive agent may then be positioned between the first and second thin film layers, and the multilayer thin film structure subsequently sealed and furled, as described above.

Methods of Local Delivery of Bioactive Agent

Also provided is a method of localized delivery of a bioactive agent to a tissue. In some embodiments, the method includes administering to a subject a multilayer thin film medical device, as described above. By administering is meant positioning the device at a location in the body of a subject. Positioning the device in a subject may be carried out by placing the device (e.g., placing surgically, injection by syringe or delivery by catheter, placing orally in mouth) in any suitable opening, tissue, or body cavity of the subject where local delivery of the bioactive agent is desired. For example, the device may be injected in a cavity of the eye of the subject, such as the peripheral vitreous cavity of the eye. For example, the device may be positioned in any convenient space in a tissue mass. The device may have a furled structure suitable for injecting, e.g., injection by syringe.

When a furled multilayer thin film device is positioned in the subject it may contact a hydrating liquid in the subject and unfurl to produce an unfurled multilayer thin film structure. In addition, the hydrating liquid may dissolve the pore forming agent from a layer of the unfurled multilayer thin film structure to produce a porous layer that provides for release of the bioactive agent from the medical device.

In some embodiments, the subject device releases the bioactive agent in a time-controlled fashion. In this way, the therapeutic advantages imparted by the addition of the bioactive agent may be continued for an extended period of time. In some embodiments, the subject device will elute the bioactive agent to the surrounding tissue upon placement of the device in the patient for a period ranging from about 2 minutes to about 1 day or more, such as 2 days or more, 3 days or more, 7 days or more, 14 days or more, 21 days or more, or 1 month or more. In certain embodiments of the subject method, the releasing device locally delivers an effective amount of the bioactive agent over an extended period of time, e.g., 1 or more months, such as 2 or more, 3 or more, 4 or more, 5 or more, 6 or more, 9 or more or 12 or more months.

In certain embodiments of the subject method, the releasing of the bioactive agent from the medical device is a controlled release that occurs without an initial burst of bioactive agent. By "without an initial burst" is meant that the bioactive agent does not release from the device in an appreciable amount during a predetermined initial period (e.g., 1 week or less, such as 3 days or less, 1 day or less, 12 hours or less, 6 hours or less, 3 hours or less or 1 hour or less). The presence and level of an initial burst of a bioactive agent may be readily determined by one of ordinary skill in the art employing any convenient pharmacological methods. For example, less than about 50% of the bioactive agent is released in the predetermined initial period, such less than about 40%, less than about 30%, less than about 20%, less than about 10%, less than about 5%, less than about 2%, or less than about 1% of the bioactive agent.

In certain embodiments of the subject method, the releasing of the bioactive agent from the medical device is substantially zero order over an extended period of time. By "substantially zero order" is meant a release profile of the bioactive agent from the device that provides for a substantially constant release of drug, e.g., a release profile where the fraction of bioactive agent eluted from the device is substantially linear with respect to time, over an extended period of time. For example, a release profile where about 20% or less, such as about 10% or less, or 5% or less of bioactive agent is released after 10 days following administration. For example, a release profile where about 40% or less, such as about 20% or less, or about 10% or less of bioactive agent is released after 20 days following administration. For example, a release profile where about 60% or less, such as about 30% or less, or about 15% or less of bioactive agent is released after 30 days following administration. For example, a release profile where about 80% or less, such as about 40% or less, or about 20% or less of bioactive agent is released after 40 days following administration. For example, a release profile where about 80% or less, such as about 70% or less, about 60% or less, or about 50% or less of bioactive agent is released after 50 days following administration. For example, a release profile where about 90% or less, such as about 80% or less, about 70% or less, about 60% or less, or about 50% or less of bioactive agent is released after 60 days following administration. For example, a substantially zero order release profile of a bioactive agent that is a protein, where the protein is released from the device at a rate of about 20 microgram/month to about 1.0 mg/month over an extended period of time. For example, a substantially constant release of an effective amount of a protein bioactive agent (e.g., interferon) at about 0.5 mg/day over an extended period of time.

The bioactivity or stability of the bioactive agent may be maintained in the device after administration for an extended period of time. For example, the bioactivity of a bioactive agent (e.g., an antibody therapeutic) per unit amount of the agent that is eluted from the device is substantially constant over an extended period of time, e.g., 1 month or more, 2 months or more, 70 days or more, 3 months or more, 6 months or more, or 1 year or more. Accordingly, the subject devices provide for a significant improvement in maintaining the bioactivity of a bioactive agent over an extended period of time, e.g., 1 month or more, 2 months or more, 70 days or more, or 3 months or more, 6 months or more, or 1 year or more as compared to the bioactivity of the bioactive agent that is similarly positioned in a subject but not present in the multilayer thin film device.

In certain embodiments of the subject method, the device is administered intravitreally in the eye(s) of a subject, for example, the device is administered by intravitreal injection. In other embodiments, the device is administered subretinally to a subject. In other embodiments, administering the subject device to the eye of a patient include administration to one or more of the anterior chamber, vitreous, suprachoroidal space, sub-conjunctival space of the eye(s) of a patient.

In certain embodiments, the bioactive agent is a protein therapeutic, such as an anti-VEGF antibody. In certain embodiments, the hydrating liquid in the subject is vitreous fluid.

In certain embodiments of the subject method, the insertion is in the anterior chamber of the eye. In certain embodiments, the bioactive agent is a small molecule therapeutic, such as latanoprost for glaucoma treatment.

In certain embodiments of the subject methods, the multilayer thin film medical device further comprises a third nanostructured porous layer positioned between the first layer and the reservoir of the bioactive agent, wherein the third nanostructured porous layer includes a biodegradable polymer (e.g., PCL). In certain embodiments, the third nanostructured porous layer has an average pore size of between about 2 nm and about 50 nm.

In certain embodiments of the subject method, the second non-porous layer is biodegradable. In certain embodiments, the second non-porous layer includes PCL.

Also provided is a method of treating a patient in need of a medical device for drug delivery comprising the steps of selecting the medical device. Exemplary devices include, cardiovascular devices, neurological devices, neurovascular devices, gastrointestinal devices, muscular devices, ocular devices, and the like. In this embodiment, the term "selecting" means, for example, purchasing, choosing, or providing the device rather than preparing the device.

The methods and devices disclosed herein can be used for both human clinical medicine and veterinary applications. Thus, the subject or patient to whom the device is administered can be a human or, in the case of veterinary applications, can be a laboratory, agricultural, domestic, or wild animal. The subject devices and methods can be applied to animals including, but not limited to, humans, laboratory animals such as monkeys and chimpanzees, domestic animals such as dogs and cats, agricultural animals such as cows, horses, pigs, sheep, goats, and wild animals in captivity such as bears, pandas, lions, tigers, leopards, elephants, zebras, giraffes, gorillas, dolphins, and whales.

In some embodiments, the release kinetics of the one or more bioactive agents that are eluted from the subject devices provide for a substantially constant local delivery of a therapeutically relevant dosage of the bioactive agent. In certain embodiments, the release kinetics of the bioactive agent is substantially zero order over an extended period of time. In some embodiments, a composition of the subject device may be designed to provide for two elution profiles, e.g., a first early elution of bioactive agent from a first layer, and a second later elution of bioactive agent from a second layer. In some embodiments, the bioactive agent is stable in the subject devices over an extended period of time. In certain embodiments, the activity of the bioactive agent in the reservoir is maintained following administration in vivo. For example, the activity of the bioactive agent in the reservoir is maintained over a period of about 30 or more days, such as about 60 or more days, 70 or more days, 3 or more months, about 4 or more months, about 5 or more months, about 6 or more months, about 8 or more months, about 10 or more months, or about 12 or more months.

Kits

Kits for use in connection with the subject devices and methods are also provided. The above-described multilayer thin film devices, comprising one or more bioactive agents for elution to the surrounding tissue upon placement in a subject, can be provided in kits, with suitable instructions in order to conduct the methods as described above. In certain embodiments, the kit contains a subject device that has a furled structure. In some embodiments, the device has an unfurled structure and the kit includes instructions for furling the device so that the device may be positioned in a subject by syringe.

The subject kits may also include a syringe capable of delivering the device to a subject, e.g., by injection of a carrier fluid containing the device having a furled structure. The syringe has a gauge (e.g., 20 gauge) suitable for in vivo injection of the device. In some embodiments, the syringe is pre-loaded with a carrier fluid that contains the device, where the device is maintained in a furled structure in the carrier fluid. In other embodiments, the kit includes a container for storing the device prior to loading of the syringe and administration to the subject, where the device can be stored having a furled or an unfurled structure. In certain embodiments, when the device is stored in the container in an unfurled state, the kit may include instructions for furling the device prior to administration, e.g., by drying under reduced vacuum. The container may optionally include a carrier fluid suitable for storing the subject device and/or administration of the device.

In some embodiments, the kit contains in separate containers materials necessary for fabricating the multilayer thin film. The kit may also include materials for administering the device to a subject. Instructions (e.g., written, tape, VCR, CD-ROM, etc.) for carrying out the methods may be included in the kit. The kit can also contain, depending on the particular method, other packaged reagents and materials (i.e. buffers and the like). The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject kits. As with the instructions, the means for obtaining the instructions and/or programming is generally recorded on a suitable recording medium.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials were used in the Examples below.

Microporous Thin Film Fabrication

Thin films were spin-cast onto a flat circular poly(dimethylsiloxane) (PDMS) (Sylgard 184, Dow Corning, Midland, Mich.) mold due to its flexibility and the delicacy of the PCL/gelatin thin films. To fabricate the PDMS mold, the base and curing agent were mixed at a 10:1 ratio, degassed under vacuum, poured onto a 3" Silicon wafer, and baked at 65° C. for 2 hours. Once cured, the PDMS was peeled from the silicon master and cut into a 35 mm diameter circle. Separate solutions of polycaprolactone (PCL) (MW 80,000, Sigma-Aldrich, St. Louis, Mo.) and gelatin (from porcine skin, Sigma-Aldrich) were constantly stirred in 0.1 g mL$^{-1}$ 2,2,2-trifluoroethanol (TFE) (Sigma-Aldrich) on a hot plate at 80° C. until dissolved. PCL and gelatin solutions were then combined into centrifuge tubes in the following volumetric ratios: 7:3, 8:2, 9:1, and 10:0 (PCL:Gelatin). To mix the PCL and gelatin together, solutions were vortexed for 30 seconds and inverted twice. This process was repeated for at least 5 minutes per solution immediately prior to casting. PCL/gelatin solutions were spin cast using a P6700 Series Spincoater (Specialty Coating Systems, Indianapolis, Ind.) at 1500 RPM for 1 minute as previously described [Steedman et al., "Enhanced differentiation of retinal progenitor cells using microfabricated topographical cues." Biomedical Microdevices 12(3) (2010) 363-369]. Thin films were carefully peeled from the PDMS mold after spin casting using forceps.

Nanoporous Thin Film Fabrication

All chemicals for nanoporous PCL fabrication were obtained from Sigma-Aldrich (St. Louis, Mo.). Nanoporous PCL films were fabricated using zinc oxide nanorod templates using techniques Zinc oxide rods were grown on glass or silicon substrates that were cleaned prior to use with a solution of sulfuric acid and hydrogen peroxide (3:1) for 30 minutes and subsequently rinsed with deionized water and dried with nitrogen. Substrates were exposed to an oxygen plasma (200 W, 0.5 mTorr) for 5 minutes prior to spin casting a zinc acetate (ZnAc$_2$) seed layer. For this, a solution of 0.75 M ZnAc$_2$ and ethanolamine in 2-methoxyethanol was cast onto clean glass or silicon substrates at 1000 rpm for 60 seconds. Substrates were annealed on a hot plate at 400° C. for 30 minutes to convert ZnAc$_2$ into ZnO. Substrates were then placed in an aqueous 5 mM ZnAc$_2$ solution at 85-90° C. for 4 hours (replacing the growth bath once), which resulted in the growth of ZnO nanorods. A 300 mg/ml solution of PCL in 2,2,2-trifluoroethanol was prepared as described above and cast onto ZnO templates at 500 rpm for 30 seconds followed by 1500 rpm for 30 seconds, which is sufficiently thick to cover the ZnO template. These substrates were heated to 130° C. on a hot plate to remove any excess solvent and to allow the PCL to intimately contact the template. ZnO templates were then etched with 10 mM H$_2$SO$_4$ until the template was removed and PCL films naturally floated off.

Thin Film Degradation Analysis

Thin films were stored in PBS under constant agitation for 5 days. Prior to imaging, samples were rinsed with deionized water and dehydrated in a vacuum oven. Samples were imaged using a mySEM scanning electron microscope (NovelX, Lafayette, Calif.) with an accelerating voltage of 1 kV. For pore area and porosity calculations, 3 thin films of each PCL:Gelatin ratio were imaged. For each thin film, 10 random areas per thin film were imaged and compiled. Pore areas were calculated using ImageJ (National Institutes of Health, Bethesda, Md.).

Multilayered Thin Film Device Fabrication

Devices were fabricated from two thin films, a non-porous PCL base layer and a microporous 9:1 PCL/gelatin top layer as illustrated in FIG. 3. PCL base layers were fabricated using a concentrated solution of PCL (0.2 g mL$^{-1}$ in TFE), which were spin cast at 1500 RPM for 2 minutes onto a silicon wafer. Lyophilized protein (1-4 mg) was placed in between the two device layers and secured on a silicon wafer. An annulus-shaped piece of PDMS was heated to 80° C. then placed on top of the two thin films. A flat stainless steel weight (170 g) was used to press down on the PDMS annulus for 30 seconds, melting and sealing the two films together. The small flat weight was used to ensure uniform sealing. Elution of BSA and IgG from thin film devices was monitored for 10 weeks and compared to elution from non-porous PCL-only devices. Three devices of each type were fabricated and analyzed per experiment.

Profilometry

Device thickness was characterized with an Ambios Technology XP-2 Stylus Profiler (Santa Cruz, Calif.). Profilometry was conducted with a scan speed of 0.01 mm sec$^{-1}$, a length of 1.5 mm and a stylus force of 0.2 mg.

Micro Bicinchoninic Acid Assay

A micro bicinchoninic acid assay (Thermo Scientific Pierce, Rockford, Ill.) was performed to quantify protein elution from PCL thin film devices. Multilayered thin films loaded with lyophilized BSA (Sigma-Aldrich) or IgG (isolated from bovine serum, Sigma-Aldrich) were placed in 5 mL of PBS in centrifuge tubes and shaken continuously at room temperature for 10 weeks. 1 mL of solution was removed during sampling and replaced with fresh PBS. Samples were read at 562 nm on a SpectraMax 190 microplate reader (Molecular Devices, Sunnyvale, Calif.). Data and linear regression analysis were performed in Excel (Microsoft, Redmond, Wash.).

Bovine IgG Enzyme Linked Immunosorbent Assay (ELISA)

A bovine IgG enzyme linked immunosorbent assay (ELISA) (Bethyl Laboratories, Inc., Montgomery, Tex.) was performed to verify the activity of eluted IgG from PCL/gelatin devices. Total protein sample concentrations were first determined with a micro bicinchoninic acid assay, and then diluted 1/100 to fall within the dynamic range of the ELISA assay. These samples were then assayed, and the resulting concentration values were compared to the previous bicichoninic acid assay results. A ratio of the two concentration values was calculated over four time points between 1 and 70 days after device construction.

Rapamycin Loaded PCL Film

Rapamycin loaded PCL film was prepared by stirring a solution of 200 mg/mL PCL in 2,2,2-trifluoroethanol (TFE) (Sigma-Aldrich) on a hot plate at 70° C. until dissolved. Rapamycin was then added to the solution at a concentration of 5 mg/mL and stirred until dissolved. The solution was then spin-cast onto a 3 inch silicon wafer at 1000 rpm for 30 seconds followed by 2000 rpm for 30 seconds. Circular sections of the film 16 mm in diameter were cut and incubated in PBS at 37 C. To sample drug release, 1 mL of solution was removed during sampling and replaced with fresh PBS. Rapamycin concentration was read at 260 nm on a SpectraMax 190 microplate reader (Molecular Devices, Sunnyvale, Calif.). Data and linear regression analysis were performed in Excel (Microsoft, Redmond, Wash.).

Example 1

Microporous Thin Film Fabrication and Degradation

Solutions of PCL and gelatin were combined, respectively, in the following volumetric ratios: 7:3, 8:2, 9:1 and 10:0. After vigorous mixing, the combined solutions were spin cast into flexible polymer thin films. Initially non-porous, thin films were exposed to PBS for 5 days to eliminate the readily soluble gelatin components of the thin films. After 5 days of degradation in PBS, thin films were imaged using scanning electron microscopy (FIG. 1). Micropores were found in all thin films containing gelatin, while PCL-only thin films showed no signs of degradation or porous architecture. Individual pore areas were quantified and are displayed in FIG. 1.

FIGS. 1A-F show images of scanning electron micrographs and corresponding pore size histograms of PCL/gelatin thin films after five days of degradation in PBS. Thin films were made from mixtures of PCL and gelatin at ratios of 7:3 (A and B), 8:2 (C and D), and 9:1 (E and F). Thin films made from PCL only did not contain any pores.

Thin films fabricated with the highest concentration of gelatin (7:3) contained a broad range of pore sizes, the smallest less than 2 µm in diameter and the largest over 30 µm in diameter (FIGS. 1A and 1B). Thin films with a medium gelatin concentration (8:2) also contained a wide range of pore sizes, although the largest pores found in these films were smaller than in the 7:3 gelatin thin films and only reached a maximum of 28 µm in diameter (FIGS. 1C and 1D). Thin films with the lowest gelatin concentration (9:1) contained much smaller pores, 95% of which were smaller than 10 µm in diameter (FIGS. 1E and 1F). Thin films fabricated without gelatin (10:0) were non-porous throughout the entire spin cast thin film surface.

Figure 2:
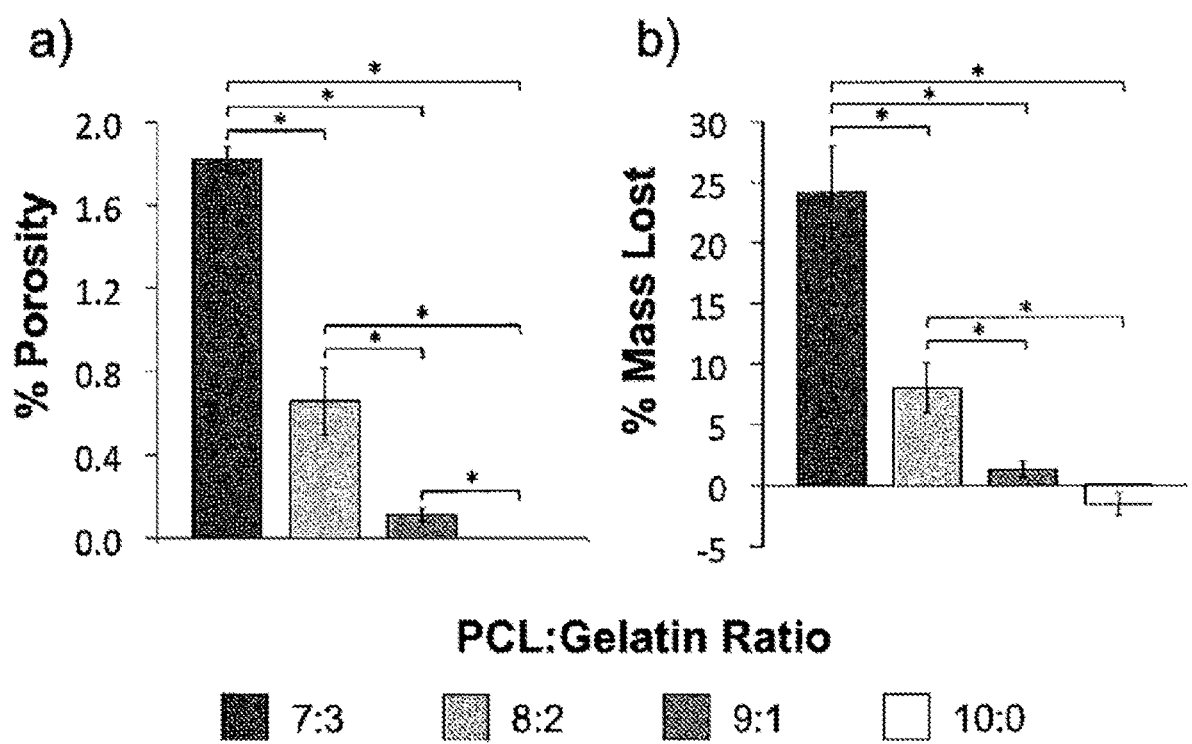
FIGS. 2A-B show graphs of the porosity and mass loss of PCL/gelatin thin films after incubation in PBS.

The percent porosity, or the pore area divided by the total area of each thin film was quantified and is shown in FIG. 2A. As the gelatin rapidly dissolves in PBS, increasing the amount of gelatin in the thin films led to more porosity after degradation. The 7:3 films were the most porous, followed by the 8:2 films, and then by the 9:1 films. Since the 10:0 films contained no gelatin, no degradation and therefore no porosity was observed.

FIGS. 2A-B illustrate the porosity and mass loss of PCL/gelatin thin films after incubation in PBS. A: Percent porosity of PCL/gelatin thin films of varying gelatin concentrations after 5 days in PBS. Overall porosity increases with gelatin concentration. B: Porosity resulting from gelatin dissolution lead to a decrease in mass. PCL swelling and salt absorption leads to a small overall increase in mass for thin films containing no gelatin. *$p<0.05$, Student-Newman, Keuls test. Error bars indicate standard deviation over three independent experiments.

The porosity found in the thin films is due to the incomplete mixing of PCL and gelatin. Although both species dissolve in TFE, combining the two solutions results in a heterogeneous emulsion that must be constantly mixed or the two solutions will separate into two immiscible liquids. Due to the high viscosity of the dissolved solutions it was empirically determined that maintenance of a consistent mixture necessitated near constant vortexing prior to spin casting. Adding increasing amounts of gelatin resulted in aggregation of the gelatin in the PCL/gelatin mixture that was not found in the 9:1 thin films.

Degradation was also quantified using the amount of mass lost after 5 days in PBS. Initial mass was determined prior to PBS immersion, while post-degradation mass was determined after 5 days in PBS and subsequent dehydration of the thin films in a vacuum oven. Results were consistent with pore area and percent porosity; the 7:3 thin films lost the most mass, approximately 25% of their initial mass, while 8:2 films lost just less than 10% on average. 9:1 thin films lost less than 5%, and films containing no gelatin gained a very small amount of mass due to the immersion in PBS (FIG. 2B). This most likely occurred due to water and salt absorption, causing the PCL areas to swell during immersion in PBS.

Multilayered Thin Film Device Fabrication and Drug Elution

PCL thin film devices were constructed from a PCL base layer and a microporous 9:1 PCL/gelatin top layer as diagramed in FIG. 3. To restrict protein elution by minimizing the porosity of the device, only 9:1 PCL/gelatin thin films were used to make the microporous top layer for all protein-loaded experimental devices. Lyophilized protein was deposited between the two thin film layers, which were then melted together using a PDMS annulus. Devices were immersed in PBS at room temperature, and elutions of BSA and IgG from the PCL/gelatin thin film devices were quantified over a 10-week period. Non-porous devices made from two PCL-only thin films were also constructed and used as controls.

FIGS. 3A-C illustrate the fabrication of the multilayered polymer thin film device. A: Lyophilized protein was contained between a non-porous PCL thin film base layer and a microporous PCL/gelatin thin film. B: A finished device ~2 mm in diameter. C: Profile of the PCL/Gelatin Device edge.

Figure 4:
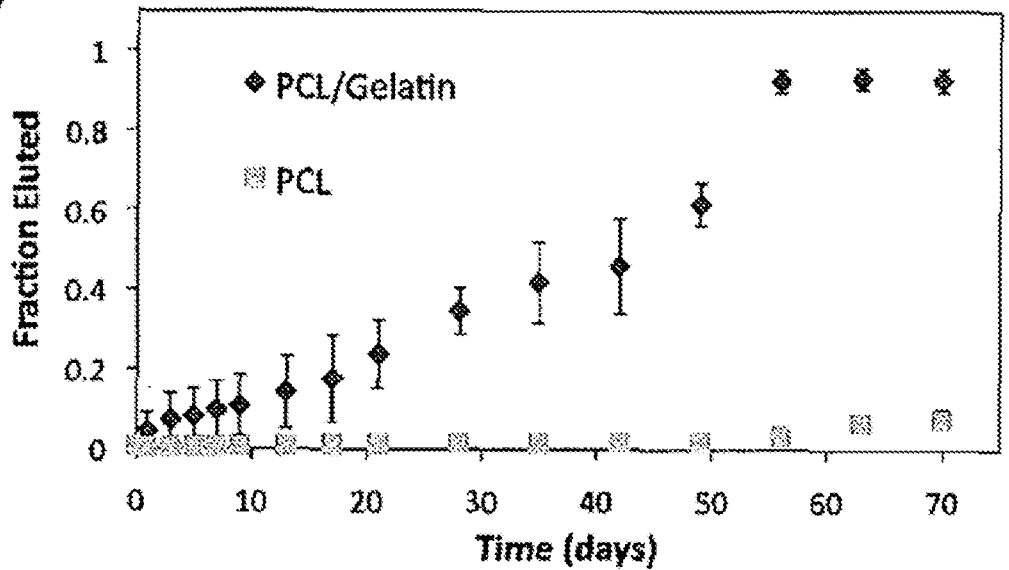
FIGS. 4A-B show the fractional elution profile of proteins ((A) BSA; (B) IgG) from PCL/gelatin and PCL-only thin film devices.
Figure 4:
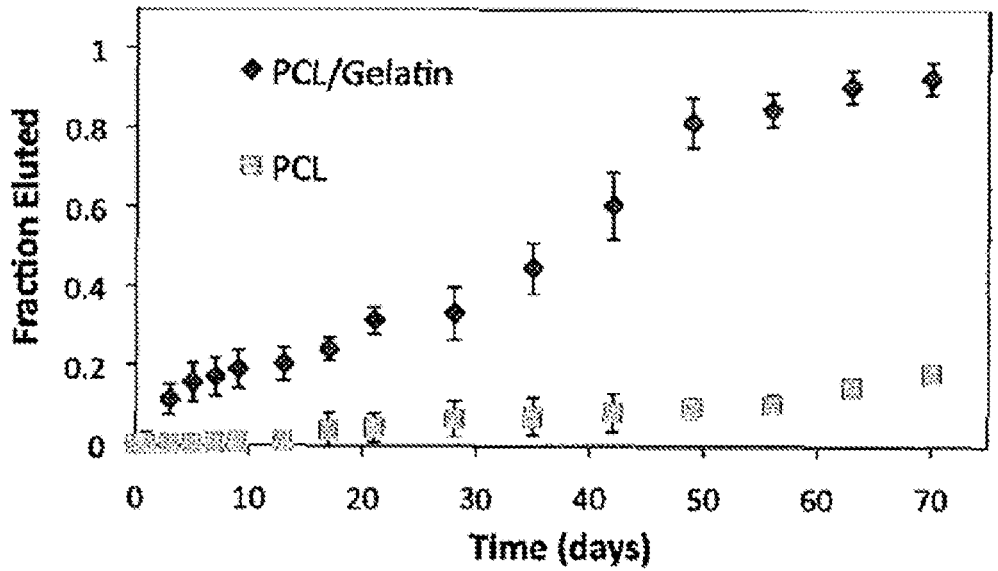

BSA elution from porous PCL/gelatin thin film devices and non-porous PCL-only thin film devices is presented in FIG. 4A. BSA eluted from the PCL/gelatin devices with zero-order kinetics for the first seven weeks, corresponding to slightly more than 60% of the ~3 mg BSA loaded into each device. Similarly, IgG elution is presented in FIG. 4B. Zero-order elution from the 9:1 PCL/gelatin devices was also achieved with IgG for the first seven weeks.

FIGS. 4A-B show the elution of protein from a PCL/gelatin thin film device. A: Fractional elution of BSA from 9:1 PCL/gelatin and PCL-only thin film devices. Zero-order elution was observed for the first 7 weeks in PCL/gelatin devices, after which device failure led to a burst release phase. PCL-only devices began to leak after 8 weeks. B: Fractional elution of IgG from 9:1 PCL/gelatin thin film devices. Zero-order elution of IgG from PCL/gelatin devices was observed for nearly all 10 weeks. Error bars indicate standard deviation over three independent experiments.

Figure 5:
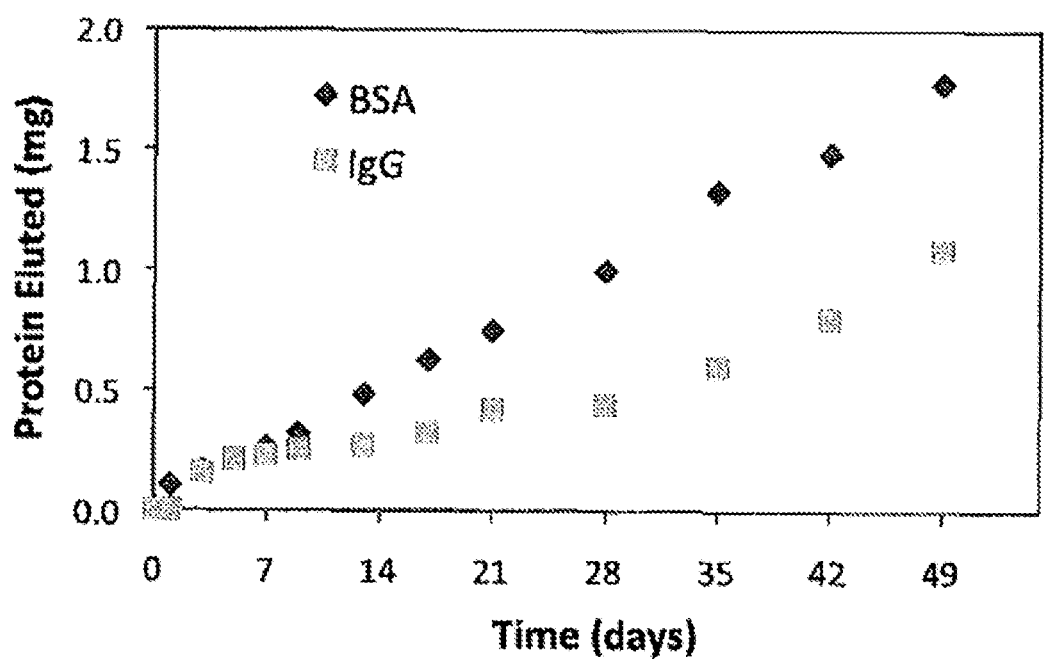
FIG. 5 shows a comparison of the rates of elution of BSA and IgG from a PCL/gelatin thin film device.

Protein elution from one BSA-loaded and one IgG-loaded PCL/gelatin thin film device is directly compared in FIG. 5. Elution for 7 weeks are displayed, corresponding to zero-order release kinetics with $R^2$ values of 0.99 and 0.94 for BSA and IgG, respectively. BSA eluted at a rate of 36 µg/day, while IgG eluted at a slower rate of 20 µg/day. IgG's slower elution rate is most likely due to its larger molecular weight (150 kDa versus 66 kDa for BSA).

FIG. 5 shows a comparison of the rates of elution of BSA and IgG from a PCL/gelatin thin film device. Larger molecular weight IgG (150 kDa) eluted at a slower rate than BSA (66 kDa). Linear regression analysis gave elution rates of 0.36 µg/day for BSA ($R^2=0.99$) and 0.20 µg/day for IgG ($R^2=0.94$).

Figure 6A:
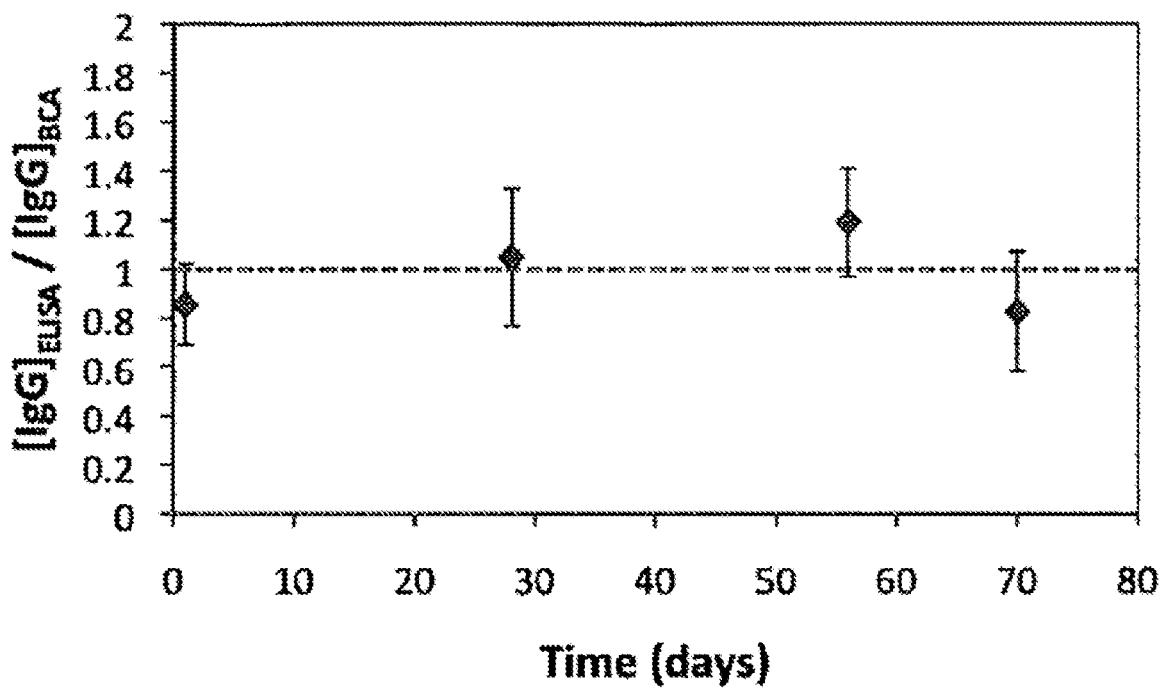
FIG. 6A illustrates that the bioactivity of IgG eluted from a PCL/gelatin thin film device is maintained over time, as determined by ELISA and BCA assays.

IgG concentration was quantified using two different assays to verify protein activity throughout the course of the experiment. FIG. 6A shows a comparison of the ratio of eluted IgG concentrations determined by ELISA and BCA assays. Concentrations were compared at 1, 28, 56, and 70 days of elution. Error bars indicate standard deviation over three independent experiments. The ratio of these two concentrations is plotted for four time points from 1 to 70 days of elution. The BCA assay quantifies total protein concentration, while the ELISA is much more specific and only quantifies bound IgG. A ratio of 1 represents an equal concentration of IgG between both assays, demonstrating that the IgG released from PCL/gelatin thin film devices is active after 70 days of elution. As the differences between the four data points are not significant and the standard deviations all fall within a ratio of 1 these results show that the IgG did not degrade over the course of the experiment.

Figure 6B:
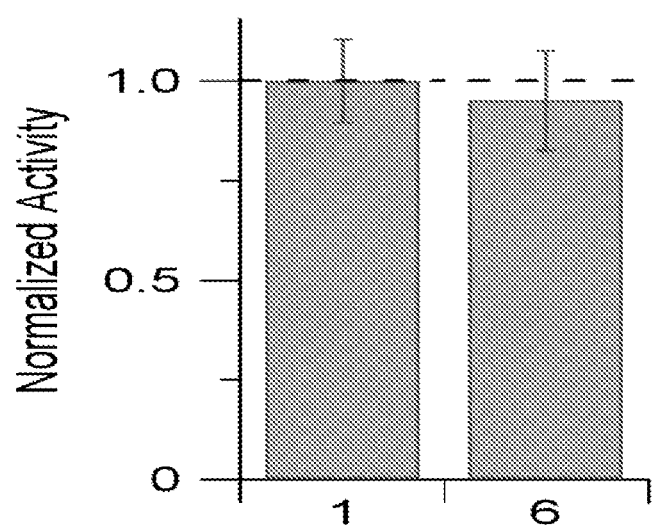
FIG. 6B illustrates in vivo activity of IgG eluted from PCL/gelatin thin film device 6 weeks-post administration.

FIG. 6B shows the activity of IgG eluted into the eye after administration of IgG containing thin film device. In vivo activity of IgG was detectable in the eye 6 weeks-post administration.

Example 2

Nanostructured Thin-Films

A template-synthesis method is used to produce nanostructures in thin biodegradable polymer films. This approach is based on templating which entails using an inorganic nanostructured surface (e.g., well-characterized rods structures of a zinc oxide ZnO material) as a template for the subsequent creation of a "soft" biopolymer thin film with desired nano-architectures. A two-step procedure is used for ZnO nanorod growth: a nanostructured seed layer is deposited and rods are grown hydrothermally from the seed layer. Through variations is seed layer deposition and hydrothermal growth condition, a variety of morphologies are produced, from random to well-oriented rods. Control of processing conditions allows nanorods to be fabricated in a wide range of diameters, lengths and inter-rod spacing.

A variety of techniques are used to deposit the target polymer onto ZnO templates.

In one example, polymers are heated above their melting point and allowed to conform to the template. Alternatively, spin casting of polymer solutions is used to generate thin films with reproducible thickness. Polycaprolactone was selected as a starting material since it has shown excellent biocompatibility and integrity within the eye. Under physiological conditions, PCL degrades by random chain scission, which gives rise to a two-phase degradation. Initially, as molecular weight decreases the physical structure is unaffected since generated polymer chains are not sufficiently soluble, but after extended degradation, there is an increased generation of monomeric degradation products, resulting in significant physical degradation.

Figure 9:
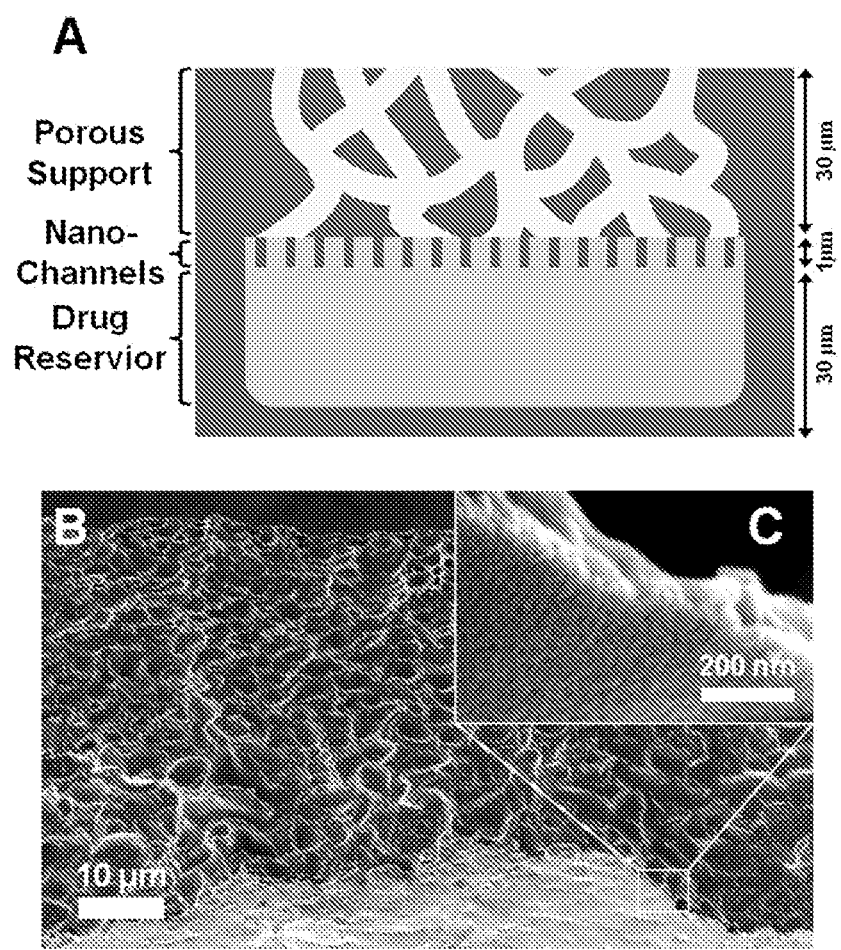
FIGS. 9 D-G depict additional configurations of exemplary multilayer thin film devices.
Figure 9:
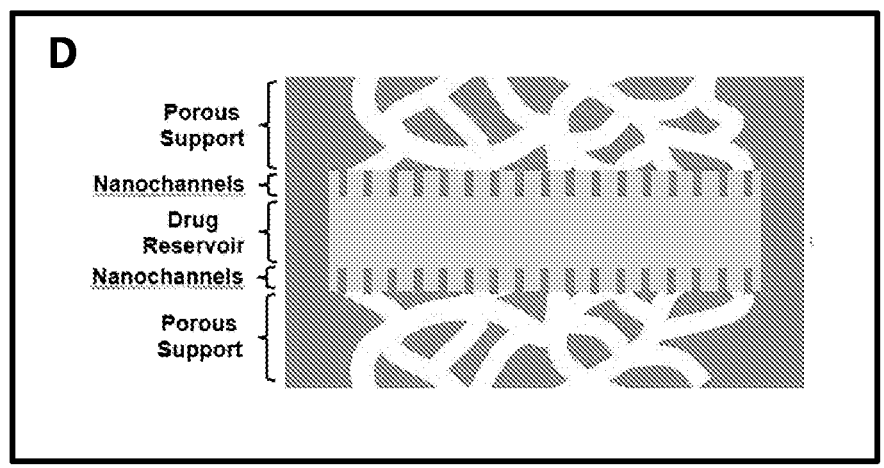
Figure 9:
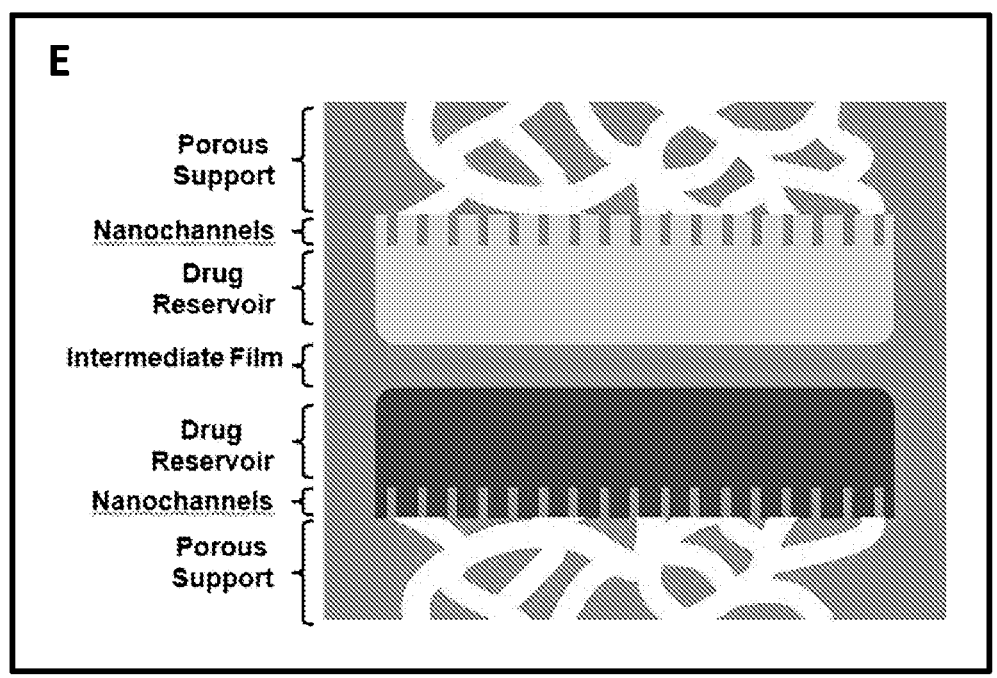
Figure 9:
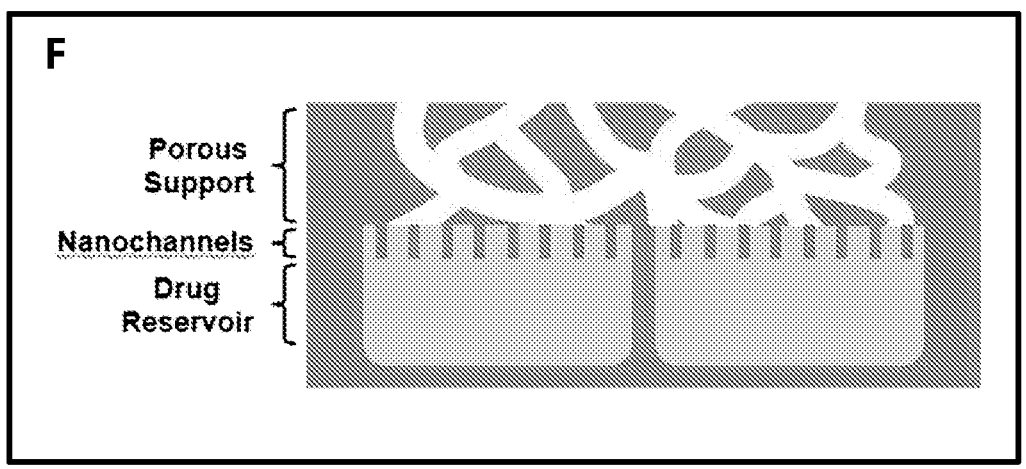
Figure 9:
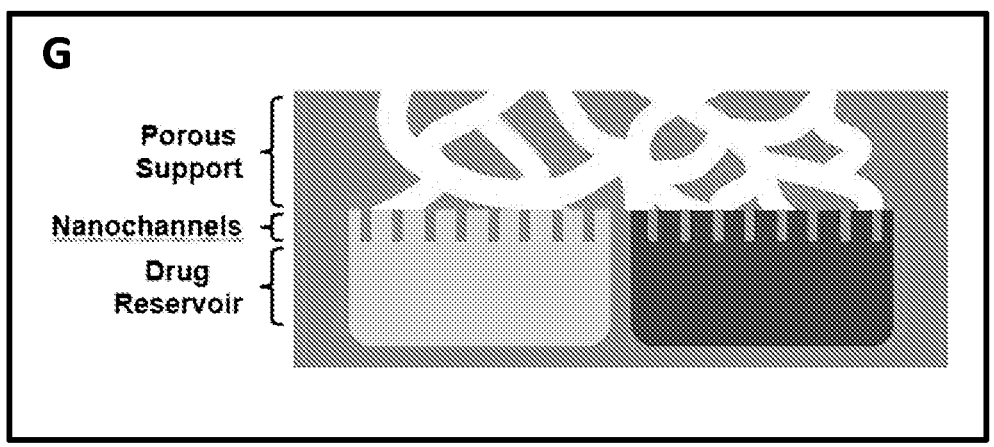

80 kDa PCL films do not degrade until after 1 year in the eye and based on the approximate MW for macroscopic degradation (8 kDa), it is estimated that PCL devices of MW between 15 and 20 kDa will start to structurally breakdown after 4 months and lose mechanical integrity by 6 months. Therefore, films are created using two exemplary different ratios (20:80 and 45:55) of 80 kDa:10 kDa PCL ($T_m$=58-63° C., $T_g$=-65 to -60° C.). We can also incorporate other degradable polymer. In addition, other films may be created, such as co-polymers of 25/75 poly(DL-lactide-co-ε-caprolactone) (25/75 DLPLCL) (amorphous, $T_g$=20° C.) or 80/20 poly(DL-lactide-co-ε-caprolactone) (80/20 DLPLCL) (amorphous, $T_g$=20° C.) to modulate the degradation rate. Finally, ZnO templates are then removed by dissolution in either acidic or strongly basic solutions. The template structure is inverted upon transfer and the subsequent polymer thin film exhibits nano-channels for drug elution and controlled release. Using this approach, ZnO rods with average rod diameter of 23±7 nm and density of approximately $10^{10}$ rods/cm² can result in a PCL film with pore sizes of 21±7 nm and a pore density of $5 \times 10^9$ pores/cm². The thickness of the film corresponds to the lengths of the nanorods that are grown, e.g., about 1 micron. Therefore, to further improve mechanical robustness, an additional porous layer is deposited prior to template removal, resulting in films with both nanoporous and microporous regions (FIGS. 9A-9C). For example, this is accomplished by casting a polymer mixture that naturally forms a porous network, such as polyethyleneglycol (PEG) and PCL, where PEG is easily dissolved in conjunction with template removal.

An exemplary process for thin film fabrication is illustrated in FIGS. 8A-8E. (FIG. 8A) A clean silicon substrate is (FIG. 8B) spin cast with a zinc oxide seed layer and nanorods are hydrothermally grown. Onto the ZnO template (FIG. 8C) PCL is spin cast followed by (FIG. 8D) spin casting a PCL and PEG solution. (FIG. 8E) rinsing with deionized water rinses the PEG-phase from the supporting layer and 10 mM $H_2SO_4$ etches the ZnO template to leave a supported nanostructured PCL thin film. FIG. 8F shows a scanning electron microscope image of a typical nanostructured PCL film. FIG. 8G shows thin layer of nanostructures on supporting membrane.

Scanning electron microscopy (SEM) is used to verify template morphology and fidelity of transfer to the polymer film. Additional characterization with electron dispersive x-ray spectroscopy (EDX) or x-ray photoelectron spectroscopy (XPS) is used to determine chemical composition and demonstrate effective removal of the ZnO template. Nanostructured membranes are then heat sealed to an impermeable capping film containing a drug reservoir (FIG. 10A).

As an example, using an inorganic template of aligned and ordered nanowires produces a nanoporous polymer membrane, as described above, an exemplary thin film was made from 80 kDa MW polycaprolactone that is curled up in its dry state and unfurls when in an aqueous environment (FIG. 7). This thin film device was fabricated to have both physical dimensions (less than 100 microns) and mechanical properties (furlability) suitable for the minimally invasive drug delivery application described herein.

Physical Properties of Thin Film Devices

Flexible soft materials were manipulated, with a particular focus on furlability to allow minimally invasive insertion into target tissues. A polycaprolactone thin film device, approximately 100 microns thick and 5 by 5 mm, is able to hold sufficient drug for 6 month delivery of anti-VEGF and still be delivered via standard injection. An extensive evaluation of exemplary devices (same size and material composition but various molecular weights) was undertaken to determine their suitability for intraocular administration Animal studies data indicated that a film composition of 45/55 80 kDa:10 kD PCL is still intact at 5 months whereas 20/80 80 kDa:10 kD PCL shows signs of degradation at 2 months. Further tuning of the parameters would result in the optimization of the degradation profile of the devices for zero-order release.

Drug Loading Approaches and Drug Payload

Because nanoporous film fabrication is independent of drug loading, several strategies are utilized to incorporate the therapeutic payload. One approach joins the membrane with an underlying film containing larger drug reservoirs. This configuration allows for a large drug carrying capacity and versatility in payload formulation, while the nanoporous membrane helps to control drug elution out of the reservoir structure.

By utilizing a further microporous supporting layer, the nanochannels are placed near the neutral mechanical plane of the device, minimizing strain on the nanopores upon rolling/unfurling. Photo- and soft lithographic techniques are used to fabricate a reservoir component of the device: photolithography is used to create a master mold on a silicon wafer by patterning a photocurable epoxy (SU-8), which determines eventual reservoir geometry. A precise master pattern is designed using CAD, and patterned on a chromium mask, to act as a stencil for optical patterning. Soft lithography is then used to cast the inverse of the master mold into an elastomer polydimethylsiloxane (PDMS). By casting the polymer of interest against the PDMS mold, the geometry of drug loaded reservoirs is transferred directly to the desired polymer, e.g., as shown in FIG. 10A. The entire device is flat, thin (e.g., about 100 or less µm), and contains multiple therapeutic reservoirs; this provides the drug payload while minimizing burst release of therapeutic upon local film rupture or failure.

The modular nature of the thin film devices allows for the reservoirs to be filled during construction of the multi-laminar biopolymer device in multiple ways. One approach is to fill the reservoir and associated nanochannels of assembled devices by submersion into a solution of drug that is directly lyophilized within the device. A second approach uses direct deposition of lyophilized drug onto the reservoir film and subsequent lamination of the films, heat sealing the films to generate the complete device. Lyophilized drug is deposited directly into device reservoirs or is incorporated within a biodegradable polymer or gel matrix. Drug loading and reservoir patterning is confirmed using fluorescently-labeled (FITC) target drug and visualized with fluorescent microscopy (FIG. 10A).

Payload Calculations and Safety Consideration

The loading requirements for a device are analyzed based upon a zero-order release profile that maintains concentration in the posterior of the eye for at least a 4 month period. For example, based on a 5 mm×5 mm thin-film with 20 nm pores, with a void space of 50% a maximal drug load in this device is 1.3 mg of lyophilized drug, with release rates as high 2 µg/day/mm$^2$ based on membrane experiments. Desired release rates depend on drug affinity, vitreous half-life, and target vitreous concentration. Based on clinical dosing, a continuous delivery device is estimated to require 4 µg/day to sustain therapeutic concentrations of, e.g., ranibizumab (50 µg/eye sustained concentration) or 480 µg of total drug for an exemplary device. Complete dose dumping for a device designed for delivery over 6 months would produce systemic drug concentration of less than 3.4 ng/ml upon failure, which falls well below the 11-27 ng/ml threshold thought to inhibit VEGF by 50%. In addition, a multi-chambered reservoir (FIG. 10) minimizes the risk that the entire drug payload could be inadvertently dumped. Based upon conservative estimates of Lucentis© half-life in the vitreous humor, a device loaded with approximately 800 µg of drug is estimated to maintain therapeutic levels for a 6 month or longer period.

Ocular Biocompatibility Studies

To assess the structural integrity and ocular tolerance of micro- and nanostructured biopolymers, in vivo safety studies were conducted in adult rabbit eyes. Devices fabricated from poly(caprolactone) (PCL) were administered into eyes of anesthetized New Zealand White rabbits (N=15) using standard microsurgical techniques. Needle injection (20 gauge) was used to insert furled biopolymer films into the vitreous. Over follow-up periods ranging from 1-6 months, regular ophthalmic examinations were performed (slit lamp, tonometry, and indirect ophthalmoscopy) for surveillance of ocular tolerability. Histologic studies on enucleated post-mortem eyes were performed at intervals of days to months to evaluate any morphologic abnormalities or device/tissue reactions. PCL films were retrieved from eyes to be evaluated by scanning electron microscopy (SEM) to determine the durability and structural integrity of devices. The PCL films were tolerated and structurally stable upon administration in the eye, in both the anterior chamber and vitreous loci. Results of the in vivo ophthalmological examinations showed no adverse signs of ocular tolerability with respect to inflammation, chronic infection, cataract, and ocular pressure. No migration of the device was observed after 6 months. Histological examination of the tissue revealed no cellular inflammation or morphologic abnormalities at ocular sites, including the retina trabecular meshwork and the specific sites of anatomic residence of the devices following administration. Device/tissue responses such as fibrosis, gliosis, or hemorrhage were not seen.

Multilayer Thin Film Device Fabrication Apparatus

Figure 11A:
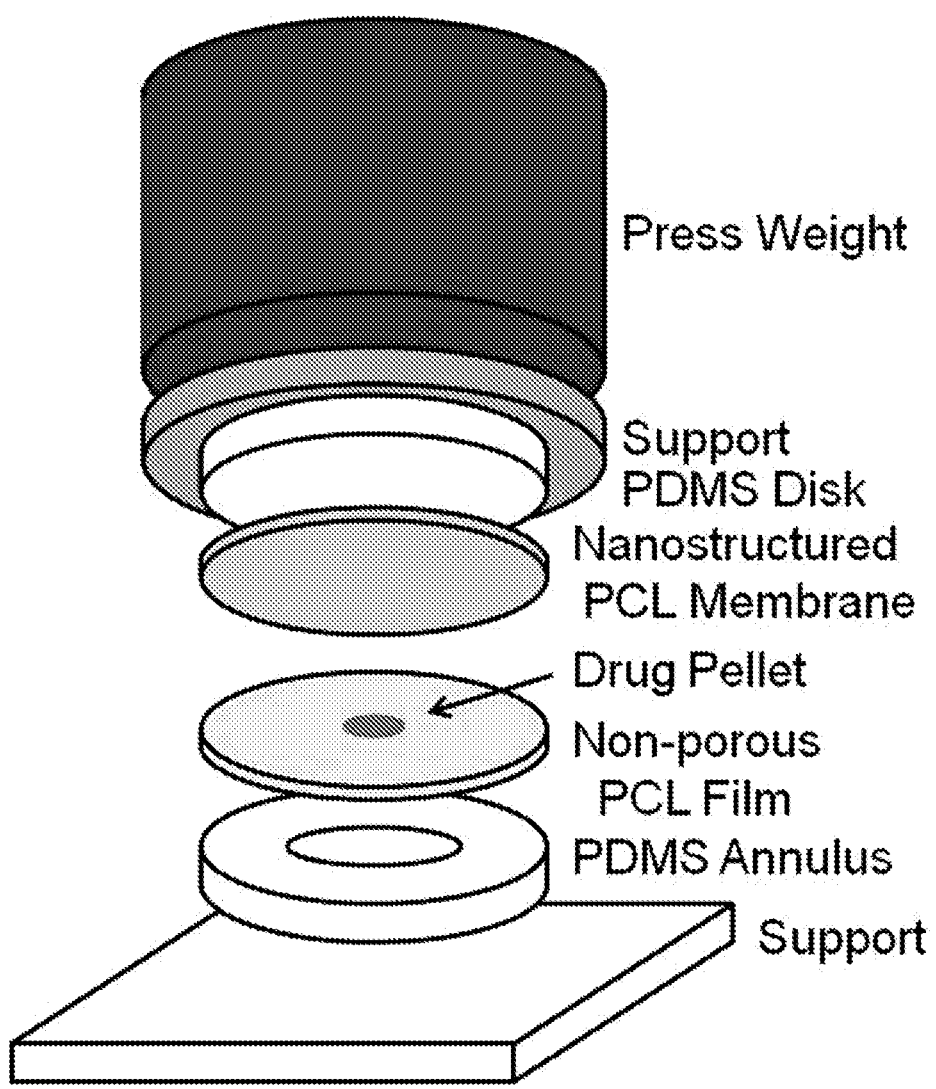
FIGS. 11A-11C depict exemplary apparatus usable for fabricating multilayer thin films disclosed herein.
Figure 11B:
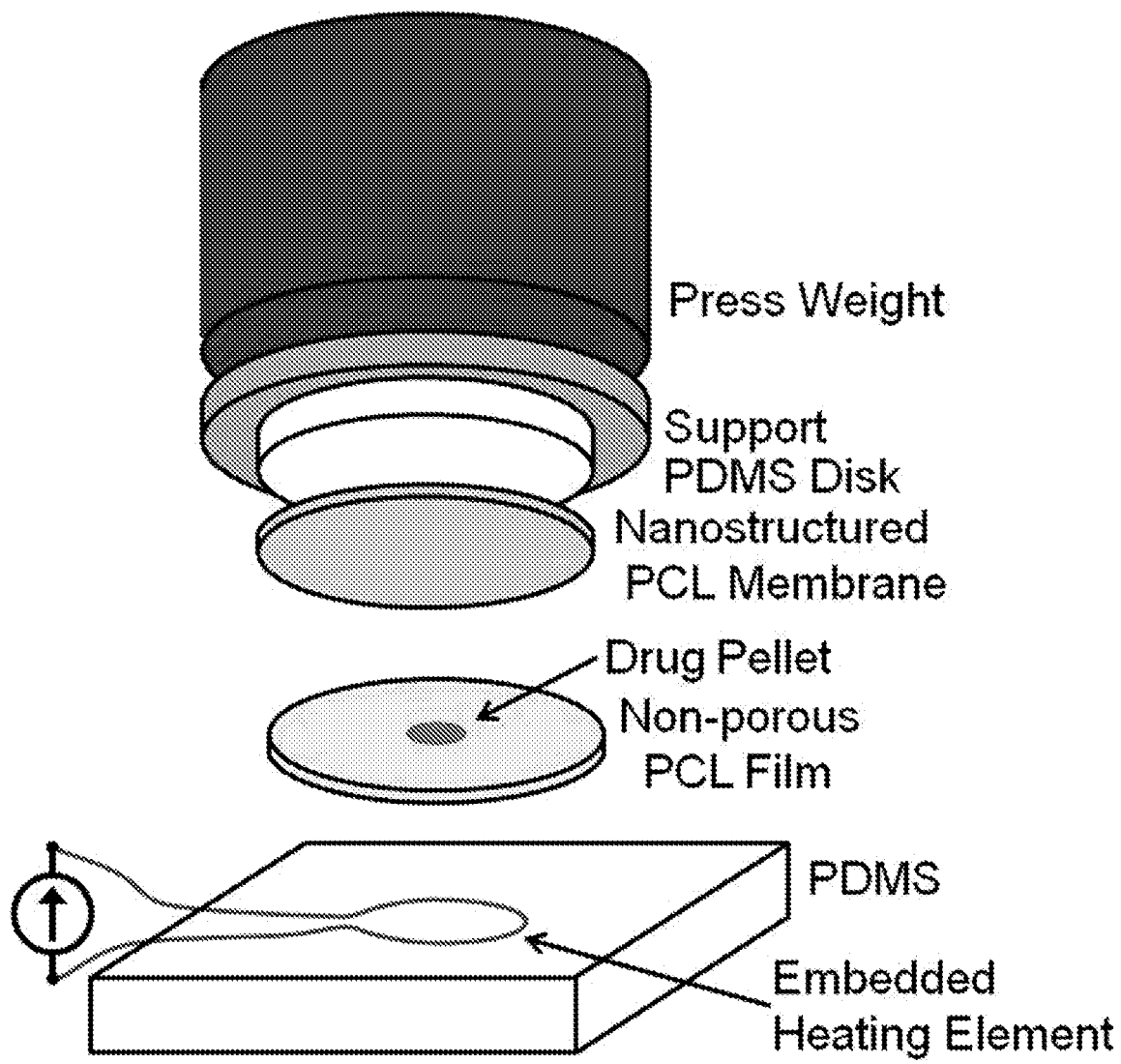
Figure 11C:
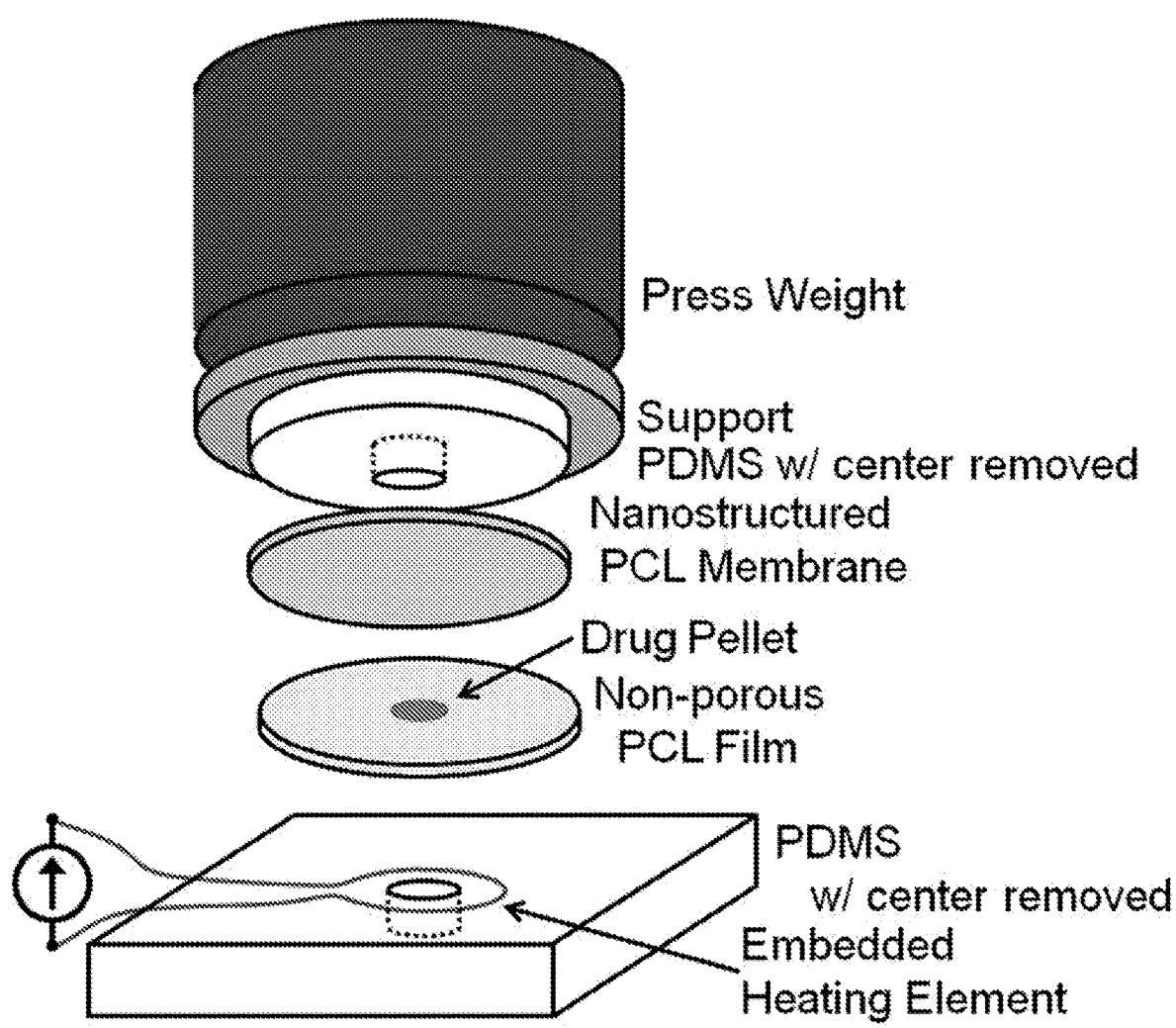

Exemplary apparatus usable for fabricating multilayer thin film disclosed here are illustrated in FIGS. 11A-11C.

FIG. 11A. The thin film device may include a flat PCL film, a drug pellet, and a nanostructured PCL film sandwiched between supporting structures using a press weight. The apparatus containing the constituent device layers is placed on a hot plate to fuse the PCL films. Because the base support is an annulus, the center of the devices experiences considerably less heating.

FIG. 11B. From the bottom up, devices consist of a flat PCL film, a drug pellet, and a nanostructured PCL film sandwiched between supporting structures using a press weight. The base of the apparatus contains a resistive heating element that seals the device from the edge in. By controlling power supplied to the heating element and duration of heating, sealing can be controlled.

FIG. 11C. From the bottom up, devices consist of a flat PCL film, a drug pellet, and a nanostructured PCL film sandwiched between supporting structures using a press weight. The base of the apparatus contains a resistive heating element that seals the device from the edge in. The center in the base and top supports are removed to minimize heating to the central portion of the device. By controlling power supplied to the heating element and duration of heating, sealing can be controlled.

Multilayer Thin Film Device for Controlled Release of Protein

Multilayer thin film devices having pore sizes in the range of 20 nm-40 nm were fabricated as described herein.

Figure 12:
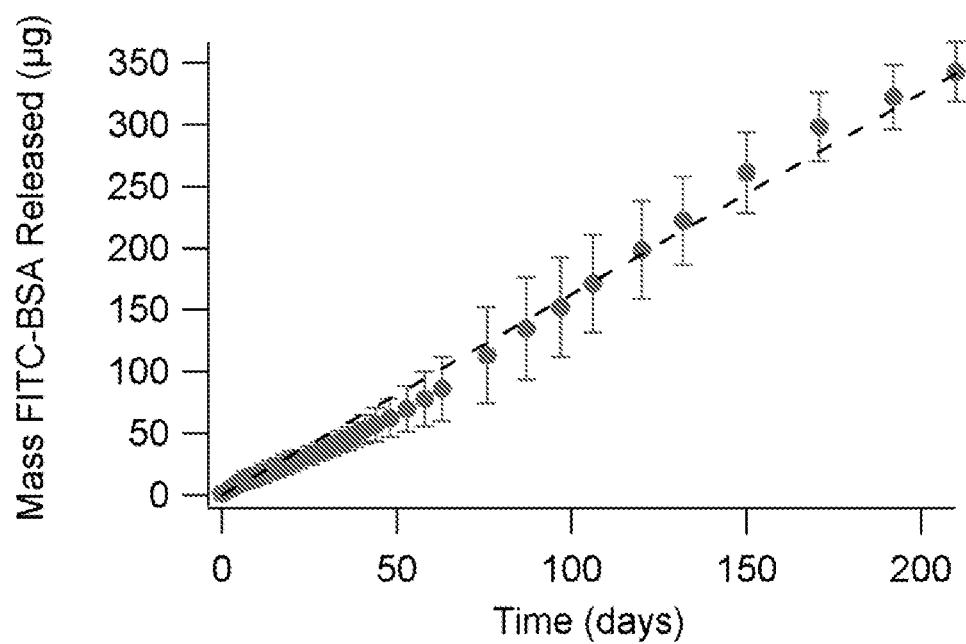
FIG. 12 shows release of protein from a multilayer thin film device as disclosed herein.

FIG. 12 shows that FITC-BSA protein was released from nanostructured PCL devices (n=3) with pore size of 20-40 nm at a release rate of 1 µg/day over a time period of 210 days.

Multilayer Thin Film Device for Controlled Release of Small Molecules

Figure 13:
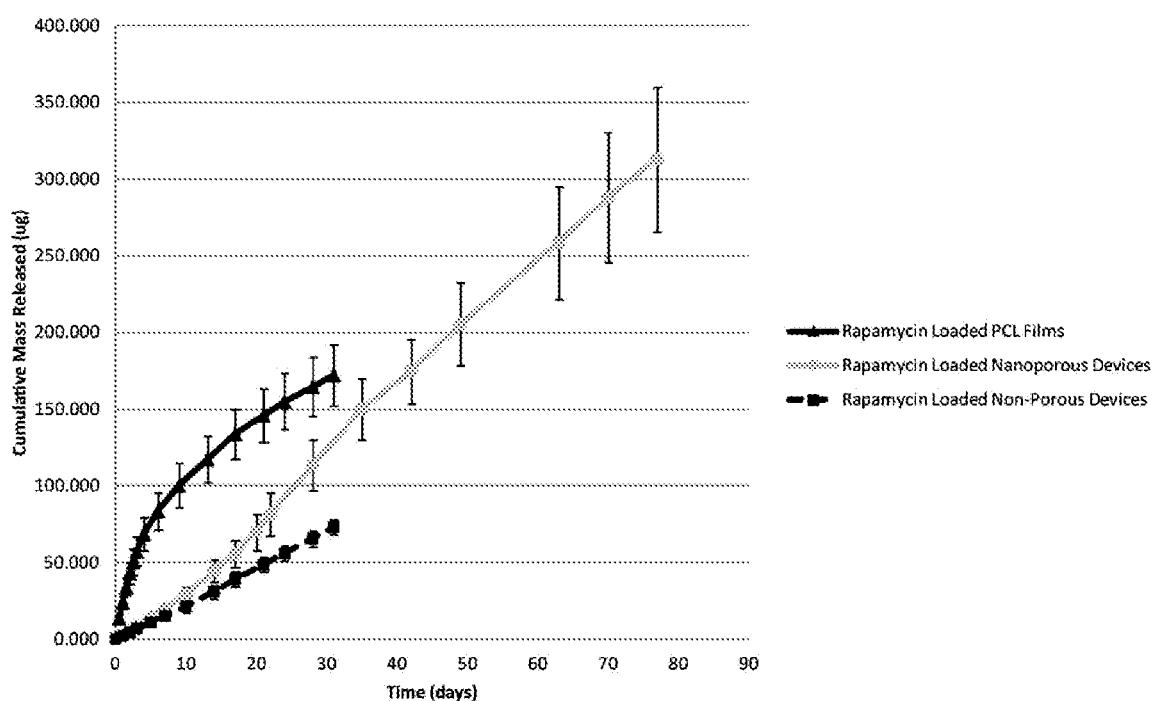
FIG. 13 illustrates the release kinetics of a small molecule (Rapamycin, molecular weight 914.172 Da) from a nanoporous thin film device (solid circles), non-porous device (solid squares) and from a PCL thin film with drug mixed in the polymer film (solid triangles). The nanoporous thin film device consisted of a supported nanostructured film (nanostructured pores of 20-40 nm and support layer pores of 1-3 microns). The non-porous film contained Rapamycin in a central reservoir. For PCL thin film, the small molecule is mixed within the polymer itself rather than contained in a reservoir.

A nanoporous multilayer thin film device was fabricated with a bioactive drug reservoir containing the small molecule, rapamycin (MW 914 Da). The release kinetics of rapamycin from this nanoporous multilayer thin film device was compared to the release kinetics of rapamycin from a non-porous device and from PCL thin film with rapamycin mixed in the polymer film FIG. 13 illustrates the release kinetics of a small molecule (Rapamycin, molecular weight 914.172 Da) from a nanoporous thin film device (solid circles), non-porous device (solid squares) and from a PCL thin film with drug mixed in the polymer film (solid triangles).

The nanoporous thin film device consisted of a first layer of supported nanostructured film (nanostructured pores of 20-40 nm and support layer pores of 1-3 microns) and a second non-porous layer, produced as described above. Rapamycin was placed on the second layer. with the nanoporous side of the first layer. The nanoporous first thin film layer was placed on the non-porous film encapsulating rapamycin between the nanoporous layer and the non-porous layer.

The non-porous device included a first layer of a non-porous film. Rapamycin was deposited on a surface of the first layer. A second non-porous layer was placed on the first layer. The two non-porous layers were sealed together encapsulating rapamycin between the non-porous layer s.

For PCL thin film, the small molecule was mixed within the polymer itself rather than contained between two layers.

Kinetics of release of the small molecule drug rapamycin (sirolimus) from the nanoporous and non-porous PCL devices were compared to the release kinetics of the same molecule from a PCL film containing the drug. FIG. 13 illustrates that the nanostructured PCL device (nanostructured pores of 20-40 nm and support layer pores of 1-3 microns) and the non-porous PCL device provide for a zero order release of the small molecule over an extended period of time. In contrast, the PCL thin film containing sirolimus releases small molecules over a shorter period of time and with first order release kinetics.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A multilayer thin film medical device, comprising:
   a first layer comprising a polymer, wherein the polymer is selected from the group consisting of poly($\varepsilon$-caprolactone) (PCL), polylactide (PLA), polyglycolide (PGA), poly(DL-lactide-co-glycolide) (PLGA), and poly(DL-lactide-co-$\vartheta$-caprolactone) (DLPLCL), wherein the first layer does not include a water soluble polymer, wherein the first layer comprises a first surface and a second surface opposite the first surface;
   a layer of lyophilized bioactive agent in absence of a polymer; and
   a second layer comprising a polymer, wherein the polymer is selected from the group consisting of poly($\varepsilon$-caprolactone) (PCL), polylactide (PLA), polyglycolide (PGA), poly(DL-lactide-co-glycolide) (PLGA), and poly(DL-lactide-co-$\vartheta$-caprolactone) (DLPLCL), wherein the second layer does not include a water soluble polymer, wherein the second layer comprises a first surface and a second surface opposite the first surface;
   wherein the bioactive agent is positioned only between the second surface of the first layer and the first surface of the second layer,
   wherein the second surface of the first layer is in contact with the first surface of the second layer at the periphery of the multilayer thin film medical device and wherein the contact extends from the periphery of the device to a periphery of the location at which the bioactive agent is positioned thereby sealing the bioactive agent inside the multilayer thin film medical device, wherein the contact does not extend to regions in interior of the device,
   wherein the bioactive agent is not positioned between the first and the second layers at the periphery of the multilayer thin film medical device,
   wherein the device has an area between 1 mm$^2$ and 36 mm$^2$,
   wherein the device has a thickness between 10 µm and 500 µm, and
   wherein the device provides a zero order release of the bioactive agent over at least 10 days following administration.

2. The multilayer thin film medical device of claim 1, wherein the first layer has a % porosity between about 20% and about 0.01%.

3. The multilayer thin film medical device of claim 1, wherein the first layer has an average pore size of 30 µm or less.

4. The multilayer thin film medical device of claim 1, wherein the device is circular and has a diameter between 2 mm and 50 mm.

5. The multilayer thin film medical device of claim 1, wherein the second layer is biodegradable.

6. The multilayer thin film medical device of claim 1, wherein the second layer comprises PCL.

7. The multilayer thin film medical device of claim 1, wherein the bioactive agent is disposed in a plurality of reservoirs located across one surface of the second layer.

8. The multilayer thin film medical device of claim 1, wherein the second layer comprises a plurality of reservoirs located across one surface of the second layer, wherein a first reservoir of the plurality of reservoirs comprises the bioactive agent and a second reservoir of the plurality of reservoirs comprises another bioactive agent.

9. The multilayer thin film medical device of claim 1, wherein the bioactive agent is a protein therapeutic, a small molecule drug, a large molecule drug or an aptamer.

10. The multilayer thin film medical device of claim 1, wherein the bioactive agent is a protein therapeutic selected from ranibizumab, bevacizumab, trastuzumab, rituximab, gentuzumab ozogamicin and cetuximab.

11. The multilayer thin film medical device of claim 1, wherein the bioactive agent is a small molecule therapeutic selected from steroids, rapamycin, or prostaglandin.

12. The multilayer thin film medical device of claim 1, wherein the first and second layers are formed from a single film folded over the bioactive agent and sealed at the periphery.

13. The multilayer thin film medical device of claim 1, wherein the polymer has a molecular weight of 80 KDa and does not start to degrade until after 1 year after in vivo placement.

14. The multilayer thin film medical device of claim 1, wherein the polymer has a molecular weight of 15 kDa-20 kDa and does not start to degrade until after 4 months after in vivo placement.

15. The multilayer thin film medical device of claim 1, wherein the first layer is a non-porous layer and the second layer is a nanoporous layer comprising pores 7 nm-50 nm in diameter, and wherein the device has a diameter of 1 mm-2 mm.

16. The multilayer thin film medical device of claim 1, wherein the first layer is a non-porous layer and the second layer is a non-porous layer and wherein the bioactive agent is a small molecule therapeutic.

17. The multilayer thin film medical device of claim 1, wherein the device comprises a furled structure or an unfurled structure.

18. The multilayer thin film medical device of claim 17, wherein the furled structure is substantially cylindrical or frusto-conical.

19. The multilayer thin film medical device of claim 17, wherein the unfurled structure comprises a substantially circular peripheral edge.

20. The multilayer thin film medical device of claim 1, further comprising a third nanostructured porous layer positioned between the first layer and the bioactive agent.

21. The multilayer thin film medical device of claim 20, wherein the second layer comprises a plurality of reservoirs located across one surface of the second layer, wherein a first reservoir of the plurality of reservoirs comprises the bioactive agent and a second reservoir of the plurality of reservoirs comprises another bioactive agent.

22. The multilayer thin film medical device of claim 1, wherein the first layer and/or the second layer comprises engineered pores.

23. The multilayer thin film medical device of claim 22, wherein the engineered pores are nanopores.

24. The multilayer thin film medical device of claim 22, wherein the engineered pores are micropores.

25. The multilayer thin film medical device of claim 1, wherein the first layer further comprises a high molecular weight polymer having a molecular weight of at least 80 kDa and a low molecular weight polymer having a molecular weight of 20 kDa or less.

26. The multilayer thin film medical device of claim 25, wherein ratio by mass of the low molecular weight polymer to the high molecular weight polymer is 3:2.

27. The multilayer thin film medical device of claim 25, wherein the ratio by mass of the low molecular weight polymer to the high molecular weight polymer is 2:3.

28. The multilayer thin film medical device of claim 1, wherein the first layer is a non-porous layer and the second layer is a microporous layer comprising pores 1-10 μm in diameter, and wherein the device has a diameter of 1 mm-2 mm.

29. The multilayer thin film medical device of claim 28, wherein the first layer comprises nanopores, wherein the device comprises a third polymer layer comprising micropores wherein the third layer is in contact with the first surface of the first layer and serves as a structural support for the first layer.

30. The multilayer thin film medical device of claim 29, wherein the second layer is a nonporous layer and wherein the nanopores are 7 nm-50 nm in diameter and the micropores are 1 μm-10 μm in diameter.

31. The multilayer thin film medical device of claim 1, wherein the first layer comprises nanopores, wherein the device comprises a third polymer layer comprising micropores wherein the third layer is in contact with the first surface of the first layer and serves as a structural support for the first layer.

32. The multilayer thin film medical device of claim 31, wherein the second layer is a nonporous layer and wherein the nanopores are 7 nm-50 nm in diameter and the micropores are 1-10 μm in diameter.

33. A multilayer thin film medical device, comprising:
a first layer consisting of a polymer, wherein the polymer is selected from the group consisting of poly(ε-caprolactone) (PCL), polylactide (PLA), polyglycolide (PGA), poly(DL-lactide-co-glycolide) (PLGA), and poly(DL-lactide-co-ε-caprolactone) (DLPLCL), wherein the first layer comprises a first surface and a second surface opposite the first surface;
a layer of bioactive agent in a lyophilized form, wherein the layer does not include a gel matrix; and
a second layer consisting of a polymer, wherein the polymer is selected from the group consisting of PCL, PLA, PGA, PLGA, and DLPLCL, wherein the second layer comprises a first surface and a second surface opposite the first surface;
wherein the bioactive agent is positioned only between the second surface of the first layer and the first surface of the second layer,
wherein the second surface of the first layer is in contact with the first surface of the second layer at the periphery of the multilayer thin film medical device and wherein the contact extends from the periphery of the device to a periphery of the layer of the bioactive agent thereby sealing the bioactive agent inside the multilayer thin film medical device, wherein the contact does not extend to regions in interior of the device,
wherein the bioactive agent is not positioned between the first and the second layers at the periphery of the multilayer thin film medical device,
wherein the device has an area between 1 mm$^2$ and 100 mm$^2$,
wherein the device has a thickness between 10 μm and 500 μm, and
wherein the device provides a zero order release of the bioactive agent over at least 10 days following administration.

* * * * *